United States Patent [19]
Los

[11] Patent Number: 4,911,753
[45] Date of Patent: Mar. 27, 1990

[54] HERBICIDAL 2-(2-IMIDAZOLIN-2-YL)FLUOROALKOXY-, ALKENYLOXY-, AND ALKYNYLOXYPYRIDINES AND QUINOLINES

[75] Inventor: Marinus Los, Pennington, N.J.

[73] Assignee: American Cyanamid Company, Stamford, Conn.

[21] Appl. No.: 242,386

[22] Filed: Sep. 9, 1988

Related U.S. Application Data

[60] Division of Ser. No. 933,656, Jan. 21, 1987, Pat. No. 4,772,311, which is a division of Ser. No. 702,098, Feb. 14, 1985, Pat. No. 4,647,301, which is a continuation-in-part of Ser. No. 616,747, Jun. 4, 1984, abandoned, which is a continuation-in-part of Ser. No. 382,041, May 25, 1982, Pat. No. 4,638,068, which is a continuation-in-part of Ser. No. 252,704, Apr. 9, 1981, abandoned, which is a continuation-in-part of Ser. No. 155,909, Jun. 2, 1980, abandoned, Ser. No. 155,910, Jun. 2, 1980, abandoned, Ser. No. 155,867, Jun. 2, 1980, abandoned, Ser. No. 155,908, Jun. 2, 1980, abandoned, and Ser. No. 155,865, Jun. 2, 1980, abandoned.

[51] Int. Cl.$^4$ .................. C07D 471/00; C07D 211/00; A01N 43/48; A01N 43/40
[52] U.S. Cl. .................................. 71/92; 546/82; 546/64; 546/15; 71/94
[58] Field of Search ............... 546/82, 64, 15; 71/94, 71/92

[56] References Cited

U.S. PATENT DOCUMENTS

| 2,863,801 | 12/1958 | Kühle et al. | 546/82 |
| 2,904,553 | 9/1959 | Sasse et al. | 546/82 |
| 3,336,326 | 8/1967 | Godefroi et al. | 546/82 |
| 3,538,104 | 11/1970 | Gruenfeld et al. | 546/82 |
| 3,542,798 | 11/1970 | Doebel et al. | 546/82 |
| 3,850,944 | 11/1974 | Tanaka et al. | 546/82 |
| 4,029,492 | 6/1977 | Cross et al. | 546/82 |
| 4,188,487 | 2/1980 | Los | 546/82 |
| 4,201,565 | 5/1980 | O'Neal | 546/82 |
| 4,302,464 | 11/1981 | LaMattina et al. | 546/82 |
| 4,314,844 | 2/1982 | Swithenbank et al. | 546/82 |
| 4,404,012 | 9/1983 | Orwick et al. | 546/82 |
| 4,459,409 | 7/1984 | Laduer | 546/82 |
| 4,474,962 | 10/1984 | Wepplo | 546/82 |
| 4,505,918 | 3/1985 | Huff et al. | 546/82 |
| 4,518,780 | 5/1985 | Barton et al. | 546/82 |
| 4,608,079 | 8/1986 | Los | 546/82 |
| 4,647,301 | 3/1987 | Los | 546/82 |
| 4,658,030 | 4/1987 | Barton et al. | 546/82 |

FOREIGN PATENT DOCUMENTS 0041623 8/1985 European Pat. Off. ............ 546/82

OTHER PUBLICATIONS

Lee et al., J. Heterocyclic Chemistry, 1971, pp. 831–834.
Lee et al., Chem. Abstr., vol. 76, Abst. No. 45290e (1972).
Suzuki et al., Chem. Abstr., vol. 83, Abst. No. 206,120m (1975).

Primary Examiner—Mary C. Lee
Assistant Examiner—Robert C. Whittenbaugh
Attorney, Agent, or Firm—John W. Hogan, Jr.

[57] ABSTRACT

The invention relates to novel difluoromethoxy-, trifluoromethoxy-, 1,1,2,2,-tetrafluoroethoxy-, alkenyloxy- and alkynyloxypyridine and quinoline compounds and a method for controlling undesirable plant species therewith.

4 Claims, No Drawings

HERBICIDAL 2-(2-IMIDAZOLIN-2-YL)FLUOROALKOXY-, ALKENYLOXY-, AND ALKYNYLOXYPYRIDINES AND QUINOLINES

This is a division of copending U.S. application Ser. No. 933,656, filed Jan. 21, 1987, now U.S. Pat. No. 4,772,311 which is a division of application Ser. No. 702,098 (now U.S. Pat. No. 4,647,301), filed Feb. 14, 1985, which is a continuation-in-part of abandoned Ser. No. 616,747, filed June 4, 1984 which is a continuation-in-part of Ser. No. 382,041 (now U.S. Pat. No. 4,638,068), filed May 25, 1982; which is a continuation-in-part of abandoned Ser. No. 252,704, filed Apr. 9, 1981, which is a continuation-in-part of Ser. Nos. 155,909, 155,910, 155,867, 155,908 and 155,865 which were all filed June 2, 1980 and are all now abandoned.

SUMMARY OF THE INVENTION

The invention is difluoromethoxy-, trifluoromethoxy-, 1,1,2,2-tetrafluoroethoxy-, alkenyloxy- and alkynyloxypyridine and quinoline compounds having the structures:

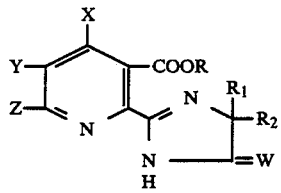

(a)

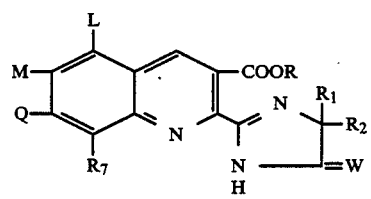

(b)

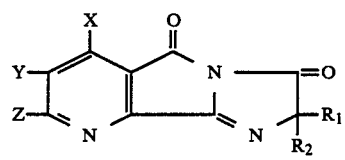

(c)

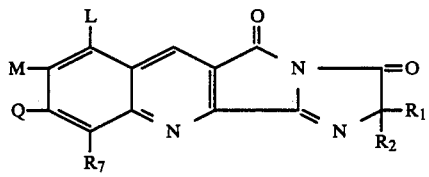

(d)

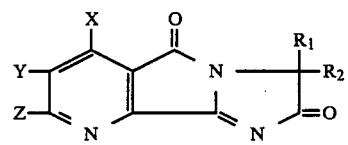

(e)

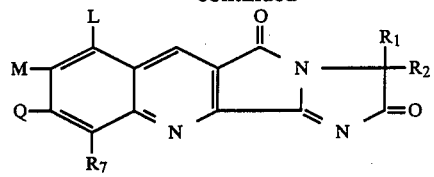

(f)

wherein
$R_1$ is $C_1$–$C_4$ alkyl;
$R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl;
R is hydrogen;

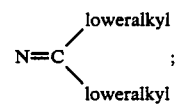

$C_1$–$C_{12}$ alkyl optionally substituted with one of the following groups: $C_1$–$C_3$ alkoxy, halogen, hydroxy, $C_3$–$C_6$ cycloalkyl, benzyloxy, furyl, phenyl, halophenyl, loweralkylphenyl, loweralkoxyphenyl, nitrophenyl, carboxyl, loweralkoxycarbonyl, cyano or triloweralkylammonium;
$C_3$–$C_{12}$ alkenyl optionally substituted with one of the following groups: $C_1$–$C_3$ alkoxy, phenyl, halogen or loweralkoxycarbonyl or with two $C_1$–$C_3$ alkoxy groups or two halogen groups;
$C_3$–$C_6$ cycloalkyl optionally substituted with one or two $C_1$–$C_3$ alkyl groups;
$C_3$–$C_{10}$ alkynyl; or a cation;
W is O or S;
X is hydrogen, halogen or methyl;
Y is hydrogen, halogen, $C_1$–$C_6$ alkyl, $C_1$–$C_4$ hydroxyloweralkyl, $C_1$–$C_6$ alkoxy, $C_1$–$C_4$ alkylthio, phenoxy, $C_1$–$C_4$ haloalkyl, nitro, cyano, $C_1$–$C_4$ alkylamino, di-$C_1$–$C_4$-loweralkylamino, $C_1$–$C_4$ alkylsulfonyl or phenyl optionally substituted with one $C_1$–$C_4$ alkyl, $C_1$–$C_4$ alkoxy or halogen, difluoromethoxy, trifluoromethoxy, 1,1,2,2-tetrafluoroethoxy, $C_3$–$C_8$ straight or branched alkenyloxy optionally substituted with one to three halogens, or $C_3$–$C_8$ straight or branched alkynyloxy optionally substituted with one to three halogens;
Z is hydrogen, halogen, $C_1$–$C_6$ alkyl, $C_1$–$C_4$ hydroxyloweralkyl, $C_1$–$C_6$ alkoxy, $C_1$–$C_4$ alkylthio, phenoxy, $C_1$–$C_4$ haloalkyl, nitro, cyano, $C_1$–$C_4$ alkylamino, di-$C_1$–$C_4$-loweralkylamino, $C_1$–$C_4$ alkylsulfonyl or phenyl optionally substituted with one $C_1$–$C_4$ alkyl or $C_1$–$C_4$ alkoxy or halogen, $C_3$–$C_8$ straight or branched alkenyloxy optionally substituted with one to three halogens, or $C_3$–$C_8$ straight or branched alkynyloxy optionally substituted with one to three halogens;
with the proviso that at least one of Y and Z is difluoromethoxy, trifluoromethoxy, 1,1,2,2-tetrafluoroethoxy $C_3$–$C_8$ straight or branched alkenyloxy optionally substituted with one to three halogens, or $C_3$–$C_8$ straight or branched alkynyloxy optionally substituted with one to three halogens;
L, M, Q and $R_7$ each represent hydrogen, halogen, $C_1$–$C_4$ alkyl, $C_1$–$C_4$ alkoxy, $C_1$–$C_4$ alkylthio, $C_1$–$C_4$ alkylsulfonyl, $C_1$–$C_4$ haloalkyl, difluoromethoxy, trifluoromethoxy, 1,1,2,2-tetrafluoroethoxy, $NO_2$, CN, phenyl, phenoxy, amino, $C_1$–$C_4$ alkylamino, diloweralkylamino, chlorophenyl, methylphenyl, phenoxy substituted with one Cl, CF₃, NO₂ or CH₃ group, C₃–C₈ straight or branched alkenyloxy optionally substituted with one to three halogens, or C₃–C₈ straight or branched alkynyloxy optionally substituted with one to three halogens; with the proviso that at least one of L, M, Q or R₇, is difluoromethoxy, trifluoromethoxy, 1,1,2,2-tetrafluoroethoxy. C₃–C₈ straight or branched alkenyloxy optionally substituted with one to three halogens. or C₃–C₈ straight or branched alkynyloxy optionally substituted with one to three halogens;

the N-oxides thereof when W is O provided that R cannot be unsaturated alkyl and Y or Z cannot be alkylamino, dialkylamino or alkylthio;

the optical isomers thereof when R₁ and R₂ are not the same;

the tautomers thereof;

the acid addition salts thereof except when R is a salt-forming cation.

In the above description of the compounds of the invention in this application, when R is a cation, it is preferably an alkali metal, alkaline earth metals, manganese, copper, iron, zinc, cobalt, lead, silver, nickel, ammonium or organic ammonium.

The compounds of the present invention may be prepared by the procedures described in the pending application for United States Letters Patent of Marinus Los, Ser. No. 382,041, filed May 25, 1982, now U.S. Pat. No. 4,638,068 incorporated herein by reference thereto.

The substituted quinolines are prepared by starting with the appropriately substituted aniline and using the reactions previously described and shown in Flow Diagram I below.

FLOW DIAGRAM I

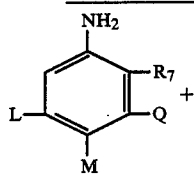

(LXXVII)

R'—CO—CH₂—COOR"        or        R"O₂C—C≡C—COOR"
(LXXVIII)                                              (LXXXVII)

| Solvent | Solvent |
| Δ | Δ |
| —H₂O | —H₂O |

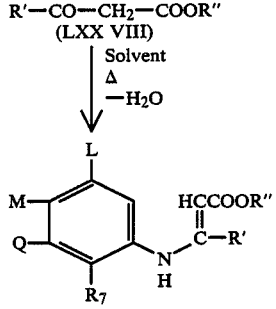

(LXXIX)                                              (LXXXIII)

Cl—CH=N⁺—(R''')₂·Cl⁻
or
Cl—CH=N⁺⊃(CH₂)ₙ'·Cl⁻
(LXXX)

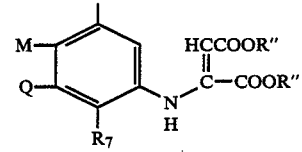

(LXXXI)                                              (LXXXIV)

NaOH
H₂O
NiO₄

1. Aqueous ethanolic NaOH Δ
2. HCl

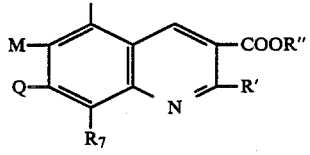

(LXXXV)

Ac₂O

FLOW DIAGRAM I

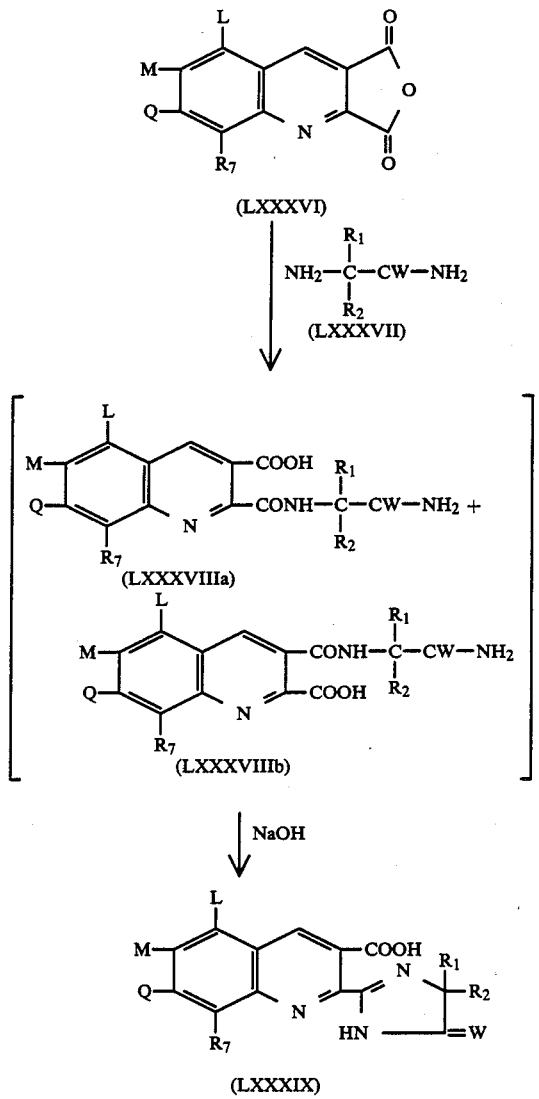

The substituted pyridines are prepared by one or both of two methods. In the first case the product can be derived by alkylation of the appropriately substituted 5-pyridinol described in the pending application. This is shown in Flow Diagram II below.

FLOW DIAGRAM II

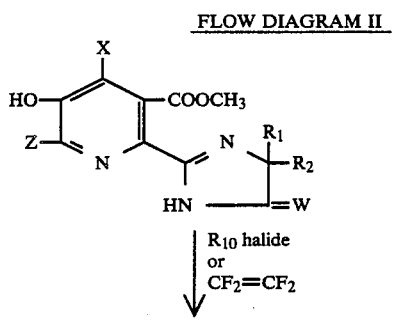

-continued
FLOW DIAGRAM II

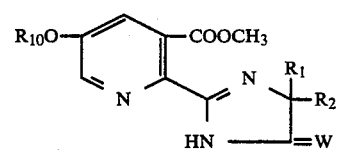

where $R_{10}$ is $CF_2H-$, $C_3-C_8$ straight or branched alkenyl or alkynyl optionally substituted with one to three halogens.

Alternatively the alkenyloxy or alkynyloxy group is introduced into the molecule prior to carboxylation as illustrated in Flow Diagram III below.

FLOW DIAGRAM III

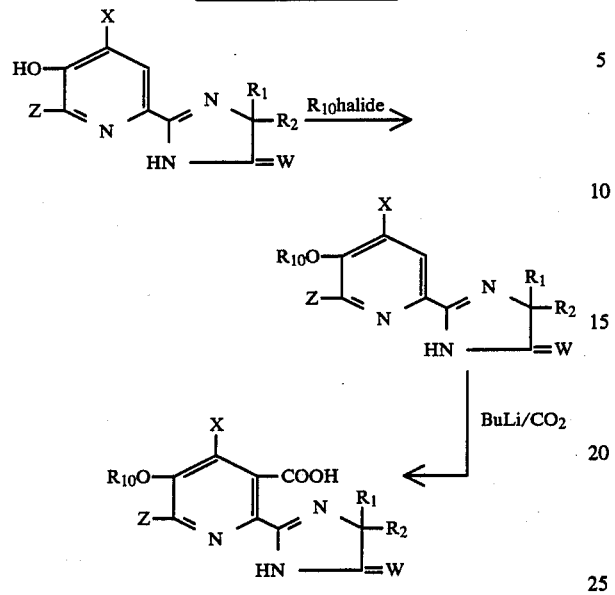

where $R_{10}=C_3-C_8$ straight or branched alkenyl or alkynyl.

By yet another modification the trifluoromethoxy group can be introduced at an earlier stage of the synthetic sequence as shown in Flow Diagram IV below.

FLOW DIAGRAM IV

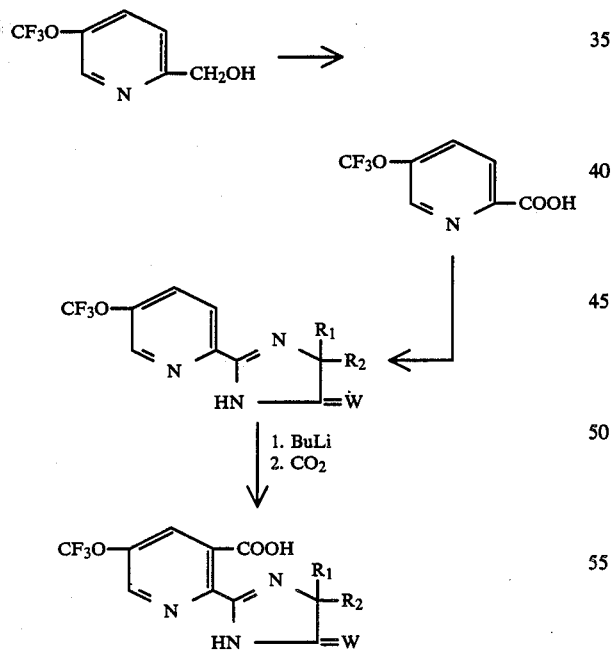

The starting material for the above sequence is described by E. J. Blanz, et al., J. Med. Chem., 13, 1124(1970). The method is described in the above identified pending application.

The pyridine derivatives in which Z=alkenyl or alkynyl groups are most readily prepared by the displacement of the compounds in which Z=Cl by the anion of the appropriate alcohol. This is shown in Flow Diagram V below.

FLOW DIAGRAM V

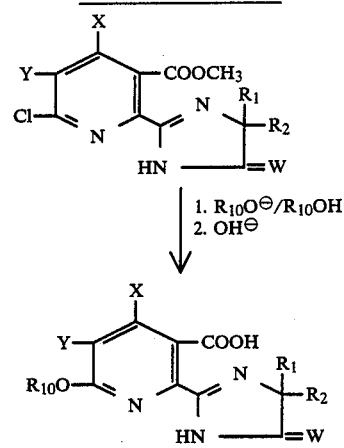

in which $R_{10}$ is $C_3-C_8$ straight alkenyl or alkynyl optionally substituted with one to three halogens. Cyclization of the appropriate acid with dicyclohexylcarbodiimide gives the 3,5-dione as shown in Flow Diagram VI below.

FLOW DIAGRAM VI

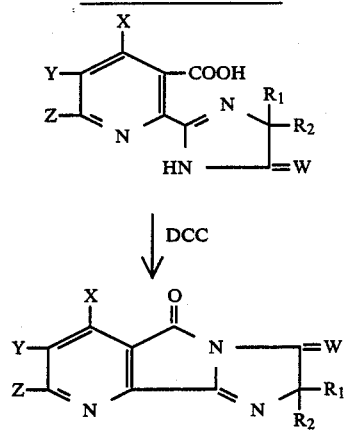

When the cyclization is carried out in acetic anhydride, the other isomer, the 2,5-dione, is obtained as shown in the Flow Diagram VII below.

FLOW DIAGRAM VII

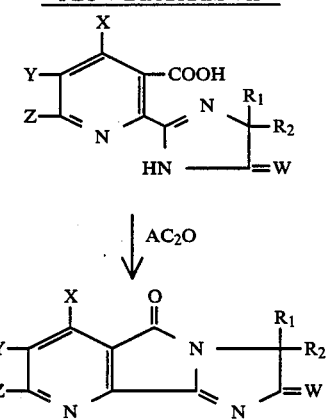

The preparation of the N-oxides can be accomplished as shown in Flow Diagram VIII below.

FLOW DIAGRAM VIII

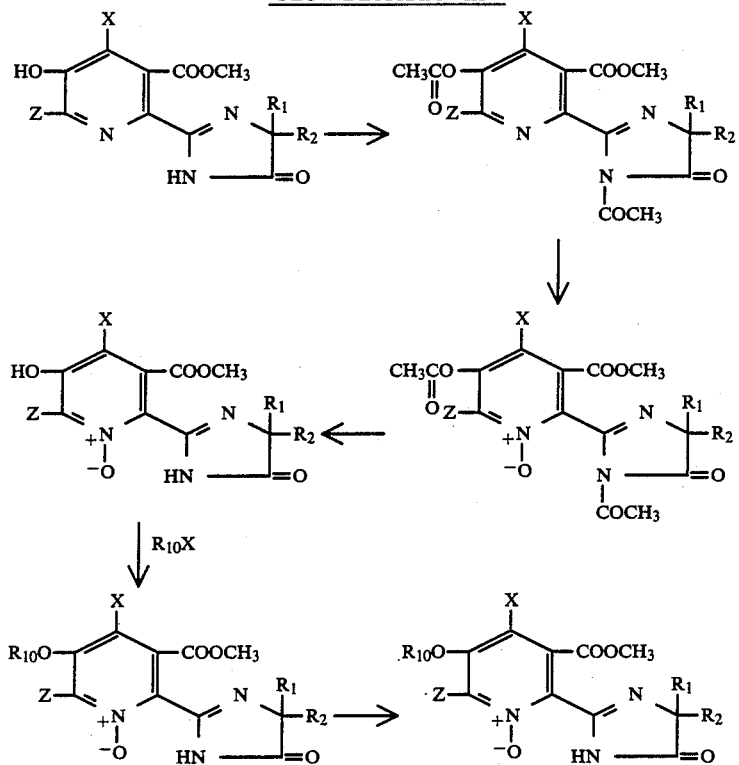

In order to prepare the compounds where Z=alkenyloxy or alkynyloxy, the chloro derivatives is converted to its N-oxide as shown below and the chloride then displaced by the appropriate alkenyl or alkynyl alkoxide followed by acid hydrolysis as illustrated in Flow Diagram IX below.

FLOW DIAGRAM IX

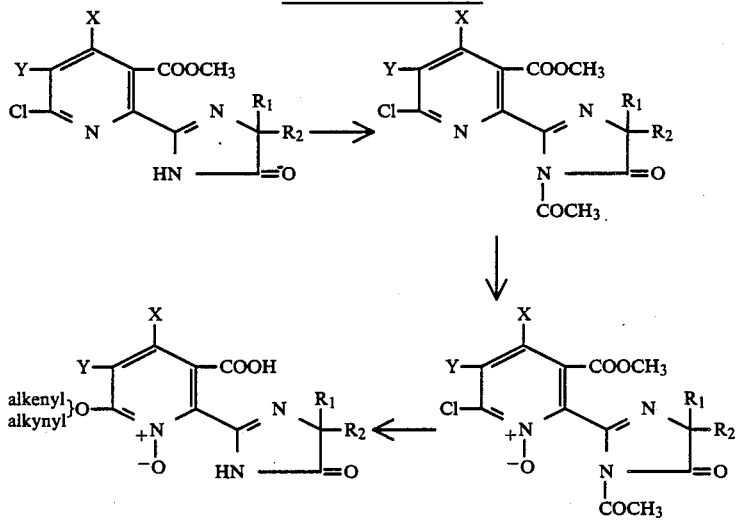

The difluoromethoxy-, trifluoromethoxy-, 1,1,2,2-tetrafluoroethoxy-, alkenyloxy-, and alkynyloxypyridine and quinoline compounds of the invention are exceedingly effective herbicidal agents useful for the control of an exceptionally wide variety of herbaceous and woody annual and perennial monocotyledonous and dicotyledonous plants. Moreover, these compounds are herbicidally effective for controlling weeds indigenous to both dry land and wet land and are unique in their effectiveness in controlling the above-said plants when applied to the foliage thereof or to soil or water containing seeds or other propagating organs of said plants such as tubers, rhizomes or stolons, at rates of from about 0.016 to 4.0 kg/ha, and preferably at rates from about 0.032 to 2.0 kg/ha.

Additionally, it has been found that some of the compounds of the invention are selective herbicides when applied to the foliage of plants or to soil containing seeds of said plants at relatively low rates of application, i.e., at from 0.016 to about 2.0 kg per hectare, depending on the compound used and crop treated, and that certain compounds are effective for increasing branching of leguminous crops and effecting early maturation of grains.

It is, of course, obvious that rates of application above the 4.0 kg/ha level can also be used to effectively kill undesirable plant species; however, rates of application of toxicant above the level necessary to kill the undesirable plants should be avoided since application of excessive amounts of toxicant is costly and serves no useful function in the environment.

Among the plants which may be controlled with the compounds of this invention are: *Elatine triandra, Sagittaria pygmaea, Scirpus hotarui, Cyperus serotinus, Eclipta alba, Cyperus difformis, Rotala indica, Lindernia pyridoria, Echinochloa crus-galli, Digitaria sanguinalis, Setaria viridis, Cyperus rotundus, Convolvulus arvensis, Agropyron repens, Datura stramonium, Alopecurus, myosuroides, Ipomoea spp., Sida sponosa, Ambrosia artemisiifolia, Eichhornia crassipes, Xanthium pensylvanicum, Sesbania exalta, Avena fatua, Abutilon, theophrasti, Bromus tectorum, Sorghum halepense, Lolium spp., Panicum dichotomiflorum, Matricaria spp., Amaranthus retroflexus, Cirsium arvense* and *Rumex japonicus*.

Since the difluoromethoxy-, trifluoromethoxy-, (1,1,2,2-tetrafluoroethoxy)-, alkenyloxy-, and alkynyloxy pyridine and quinoline derivatives, wherein $R_3$ is a salt-forming cation, are water soluble, these compounds can simply be dispersed in water and applied as a dilute aqueous spray to the foliage of plants or to soil containing propagating organs thereof. These salts also lend themselves to formulation as flowable concentrates.

Wettable powders can be prepared by grinding together about 20 to 45% by weight of a finely divided carrier such as kaolin, bentonite, diatomaceous earth, attapulgite, or the like, 45 to 80% by weight of the active compound, 2 to 5% by weight of a dispersing agent such as sodium lignosulfonate, and 2 to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5 to 25% by weight of the active ingredient in about 65 to 90% by weight of N-methylpyrrolidone, isophorone, butyl cellusolve, methylacetate or the like and dispersing therein about 5 to 10% by weight of a nonionic surfactant such as an alkylphenoxy polyethoxy alcohol. This concentrate is dispersed in water for application as a liquid spray.

When the compounds of the invention are to be used as herbicides where soil treatments are involved, the compounds may be prepared and applied as granular products. Preparation of the granular product can be achieved by dissolving the active compound in a solvent such as methylene chloride, N-methylpyrrolidone or the like and spraying the thus-prepared solution on a granular carrier such as corncob grits, sand, attapulgite, kaolin or the like.

The granular product thus prepared generally comprises about 3 to 20% by weight of the active ingredient and about 97 to 80% by weight of the granular carrier.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

Preparation of 2-(5-hydroxy-2-pyridyl)-4-isopropyl-4-methyl-2-imidazolin-5-one

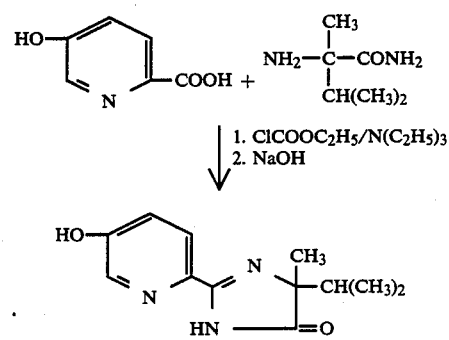

To a stirred suspension of 13.9 g 5-hydroxy-2-pyridinecarboxylic acid in 200 mL THF containing 31 mL of triethylamine at −10° C. is added 19.1 mL ethyl chloroformate. An additional 100 mL THF is added to the thick mixture. After ten minutes, a solution containing 13.4 g 2-amino-2,3-dimethylbutyramide in 50 mL THF is added dropwise. The mixture is stirred for two hours at room temperature, about 60 mL water added, and the mixture filtered and the THF removed in vacuo. The residue is extracted with ethyl acetate, the organic phase washed with brine, dried and concentrated to leave a thick orange oil.

The oil is dissolved in 95 mL of 5N NaOH and heated with stirring for three hours at 65° C. After cooling to 0° C., acetic acid is added to neutralize the base and the precipitate removed by filtration. This solid is slurried in cold methanol to give 15.2 g 2-(5-hydroxy-2-pyridyl)-4-isopropyl-4-methyl-2-imidazolin-5-one, mp 252°–254° C.

EXAMPLE 2

Preparation of 5-hydroxy-2-(4-isopropyl-4-methyl-5-oxo-2-imidazolin-2-yl)nicotinic acid

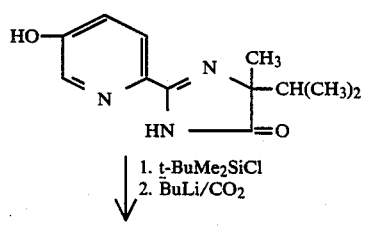

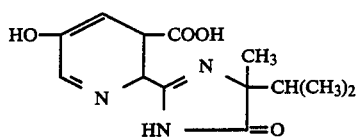

A mixture containing 20 g of the hydroxypyridylimidazolinone, 16.7 g t-butyldimethylchlorosilane and 15.65 g imidazole in 200 mL DMF is stirred at 50° C. for 16 hours. The mixture is cooled, poured into 400 mL of a saturated sodium sulfate solution and extracted with 4×250 ether. The combined extracts are washed with water and brine, dried and concentrated. Trituration with ether-hexane gives 1.3 g starting material. The filtrate is concentrated and the residue dissolved in ether. The ether solution is then washed with water, dried and concentrated to give 13.8 g crystalline residue of the t-butyldimethylsilyl ether intermediate.

To the silyl ether in 300 mL THF is added dropwise under nitrogen at $-70°$ C. with stirring 91 mL of a 0.9M solution of butyl lithium in hexane. After stirring for two and one-half hours, excess fresh solid carbon dioxide is added and stirring continued at $-70°$ C. for one hour. The mixture is stirred at room temperature for 17 hours. The THF is removed in vacuo and the residue dissolved in 300 mL water, filtered and the filtrate extracted with 3×100 mL methylene chloride. The extracts are discarded. The pH of the aqueous phase is adjusted to 3 and extracted into methylene chloride, and the organic phase separated, dried, and concentrated to give the desired title product. A larger quantity crystallized from the remaining aqueous phase to give 5-hydroxy-2-(4-isopropyl-4-methyl-5-oxo-2-imidazolin-2-yl)nicotinic acid. A pure sample has mp 255°–257° C.

EXAMPLE 3

Preparation of 5-hydroxy-2-(5-isopropyl-5-methyl-4-oxo-2-imidazolin-2-yl)nicotinate

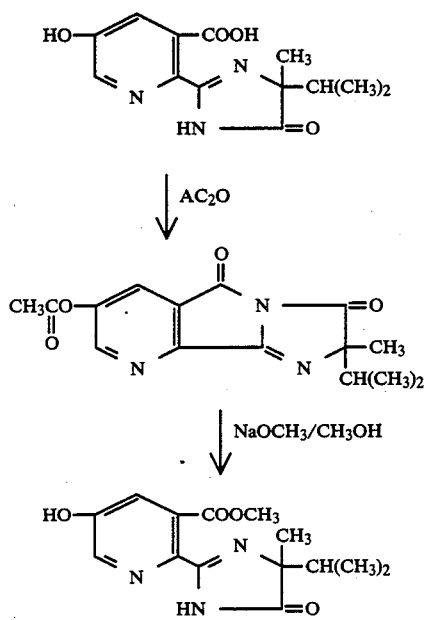

To a mixture containing 3.3 g acid and 2.05 g pyridine in 50 mL dimethoxyethane is added 3.72 g acetic anhydride and the mixture stirred overnight at room temperature under nitrogen.

The mixture is concentrated and the residue dissolved in xylene and concentrated again. This is repeated. The residue is dissolved in dry methanol, the pH of the solution adjusted to 10 with sodium methoxide and the mixture stirred overnight under nitrogen at room temperature. The pH of the solution is adjusted to 5 with acetic acid, the mixture concentrated and the residue extracted with 2×50 mL hot ether. The extracts are concentrated and the residue triturated with hexane to give the product as a light yellow solid. This product can be recrystallized from acetone-hexane to give analytically pure methyl 5-hydroxy-2-(5-isopropyl-5-methyl-4-oxo-2-imidazolin-2-yl)nicotinate, mp 200.5°–205° C.

Using essentially the same product but substituting the appropriate acid for the 5-hydroxy-2-(4-isopropyl-4-methyl-5-oxo-2-imidazolin-2-yl)nicotinic acid, there is obtained the following methyl esters.

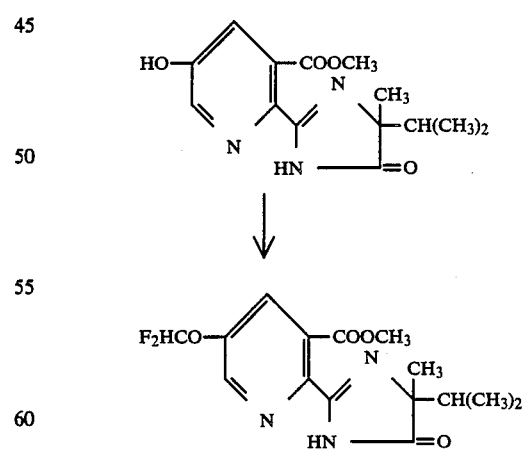

| $R_1$ | $R_2$ | Y | Z | mp °C. |
|---|---|---|---|---|
| CH₃ | CH(CH₃)₂ | H | OCH₂—CH=CH₂ | 117–119 |
| CH₃ | CH(CH₃)₂ | H | OCH₂—C≡CH | |
| CH₃ | CH(CH₃)₂ | OCH₂C≡CH | H | 83–84 |
| CH₃ | CH(CH₃)₂ | OCH₂C=CH₂ | H | 103–105 |

EXAMPLE 4

Preparation of methyl 5-difluoromethoxy-2-(4-isopropyl-4-methyl-5-oxo-2-imidazolin-2-yl)nicotinate Into a solution containing 1.25 g methyl 5-hydroxy-2-(4-isopropyl-4-methyl-5-oxo-2-imidazolin-2-yl)nicotinate and 1.40 g sodium methoxide in 50 mL absolute methanol at 50° C. is passed through a dispersion tube, chlorodifluoromethane for one hour. The mixture is cooled to 5° C. and the pH adjusted to 5 with 2N methanolic HCl. The solution is filtered and the filtrate concentrated in vacuo. The residue is extracted with 2×100 mL ether, the extracts combined, dried and concentrated. The residue is chromatographed on silica gel using ether as the eluant to give the product, analytically pure methyl 5-difluoromethoxy-2-(4-isopropyl-4-methyl-5-oxo-2-imidazolin-2-yl)nicotinate as a white crystalline solid, mp 104°–105° C.

Using essentially the same procedure but substituting the appropriate methyl 5-hydroxy-2-(4,4-dialkyl 5-oxo-2-imidazolin-2-yl)nicotinate and using either chlorodifluoromethane or tetrafluoroethylene, the compounds are prepared.

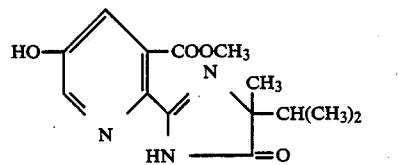

| R₁ | R₂ | W | R' | mp °C. |
|---|---|---|---|---|
| CH₃ | CH(CH₃)₂ | O | CF₂CHF₂ | 90–92 |
| CH₃ | C₂H₅ | O | CHF₂ | |
| CH₃ | Cyclopropyl | O | CHF₂ | |

EXAMPLE 5

Preparation of methyl 2-(4-isopropyl-4-methyl-5-oxo-2-imidazolin-2-yl)-5-(2-propynyloxy)nicotinate

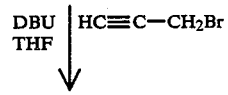

DBU | HC≡C—CH₂Br
THF

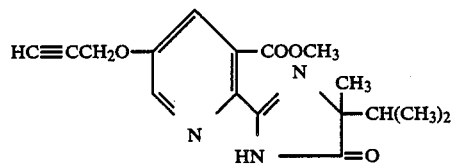

To a stirred solution containing 3.5 g hydroxypyridine and 1.55 g propargyl bromide in 100 mL THF under nitrogen is added 2.0 g DBU (1.8-diazabicyclo[5.4.0]undec-7-ene). The mixture is heated at 50°–55° C. for three hours, poured into water and extracted with 2×200 mL ether. The extract is dried and concentrated to give a crude product, which is chromatographed on silica gel. Elution with ether-hexane and pure ether gave the product which was recrystallized from ether-hexane to give analytically pure methyl 2-(4-isopropyl-4-methyl-5-oxo-2-imidazolin-2-yl)-5-(2-propynyloxy)nicotinate, mp 83°–84° C.

Utilizing essentially the same procedure but substituting the appropriate halide for propargyl bromide, the following compounds were prepared.

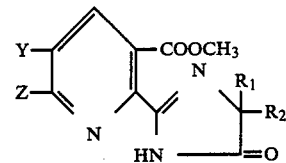

| R₁ | R₂ | Y | Z | mp °C. |
|---|---|---|---|---|
| CH₃ | CH(CH₃)₂ | —OCH₂—CH=CH₂ | H | 103–105 |
| CH₃ | CH(CH₃)₂ | —OCH₂—C=CH₂<br>　　　　　｜<br>　　　　　CH₃ | H | 105–107 |
| CH₃ | CH(CH₃)₂ | —OCH₂—C=CH₂<br>　　　　　｜<br>　　　　　Cl | H | 126–127.5 |
| CH₃ | C₂H₅ | —OCH₂—CH=CH₂ | H | |
| CH₃ | CH(CH₃)₂ | —OCH₂—C=CHCl<br>　　　　　｜<br>　　　　　Cl | H | |
| CH₃ | CH(CH₃)₂ | —OCH₂—C=CCl₂<br>　　　　　｜<br>　　　　　Cl | H | |
| CH₃ | CH(CH₃)₂ | —OCH₂CH=CHCH₃ | H | 92–95 |

EXAMPLE 6

Preparation of 5-(difluoromethoxy)-2-(4-isopropyl-4-methyl-5-oxo-2-imidazolin-2-yl)nicotinic acid

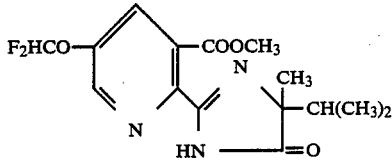

↓

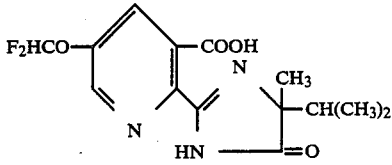

To a solution containing 400 mg methyl ester in 20 mL methanol is added 1.5 mL 2N NaOH and the mixture stirred at 40°–45° C. for two hours. The pH of the solution is adjusted to 4 with 6N H₂SO₄ and extracted twice with 200 mL CH₂Cl₂. The organic phases are combined, dried and concentrated to give the product as a white powder. The 5-(difluoromethoxy)-2-(4-isopropyl-4-methyl-5-oxo-2-imidazolin-2-yl)nicotinic acid can be recrystallized from methylene chloride-hexane to give analytically pure material mp 184°–186° C.

Using essentially the same procedure but substituting the appropriate methyl ester for the 5-difluoromethoxy derivative, there are prepared the following acids:

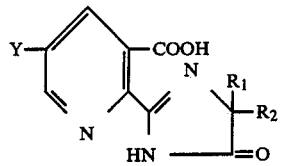

| R₁ | R₂ | Y | mp °C. |
|---|---|---|---|
| CH₃ | CH(CH₃)₂ | OCH₂—CH=CH₂ | 98–101 |
| CH₃ | CH(CH₃)₂ | OCH₂—C≡CH | 166–167 |
| CH₃ | C₂H₅ | OCH₂—CH=CH₂ | |
| CH₃ | CH(CH₃)₂ | OCH₂—C=CH₂<br>\|<br>Cl | 167–168 |
| CH₃ | CH(CH₃)₂ | OCH₂—C=CH₂<br>\|<br>CH₃ | 141–142 |
| CH₃ | CH(CH₃)₂ | OCH₂—CH=CHCl | |
| CH₃ | CH(CH₃)₂ | OCF₂CF₂H | 124–126 |
| CH₃ | CH(CH₃)₂ | OCH₂CH=CHCH₃ | 108–109 |

EXAMPLE 7

Preparation of 2-(5-isopropyl-5-methyl-4-oxo-2-imidazolin-2-yl)-6-(2-propynyloxy)nicotinic acid

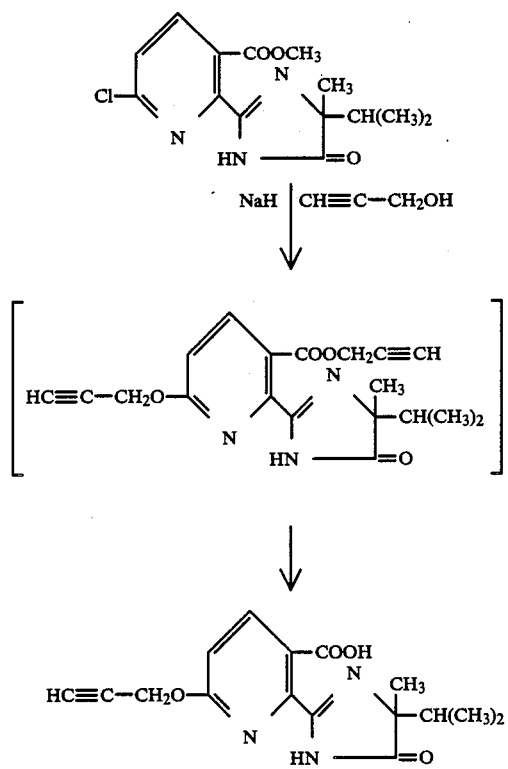

To a 100 mL propargyl alcohol at 5° C. under nitrogen is added portionwise, with stirring and cooling, 1.44 g of a 50% suspension NaH in mineral oil. The resulting solution is added to 3.11 g of the chloropyridine and the mixture heated under nitrogen, on the steam bath for 16 hours. The mixture is concentrated in vacuo, 100 mL toluene added and again concentrated. The residue is dispersed in 100 mL water and extracted with 2×100 mL CH₂Cl₂. The aqueous phase is cooled to 5° C., acidified with H₂SO₄ to pH 3 and extracted with 3×100 mL CH₂Cl₂. All the organic extracts are combined, dried and concentrated to give a residue consisting of a mixture of ester and acid.

The mixture is dissolved in 5 mL methanol, 5 mL 2N NaOH and 5 mL water and stirred at room temperature for 16 hours. The mixture is extracted with 50 mL ether, the aqueous phase acidified to pH 3 with H₂SO₄ and extracted with 2×50 mL CH₂Cl₂. The CH₂Cl₂ extracts are combined, dried and concentrated. The residue is triturated with ether to give the product as a light orange solid which is recrystallized from acetonitrile to give analytically pure 2-(5-isopropyl-5-methyl-4-oxo-2-imidazolin-2-yl)-6-(2-propynyloxy)nicotinic acid, mp 195°–198° C.

Using essentially the same conditions but substituting the appropriate alcohol for propargyl alcohol, the following 6-substituted pyridines are prepared.

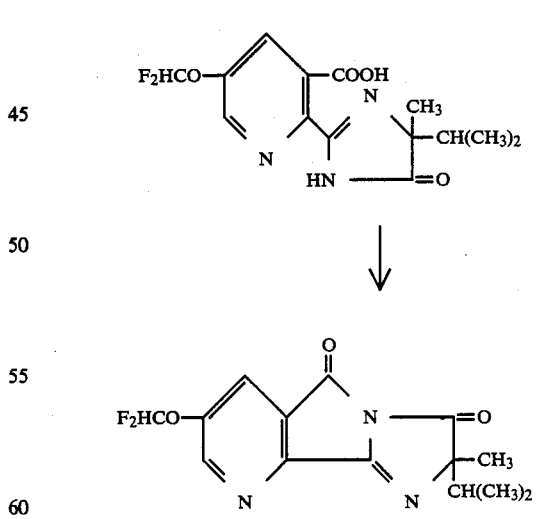

| R₁ | R₂ | Z | mp °C. |
|---|---|---|---|
| CH₃ | CH(CH₃)₂ | OCH₂—CH=CH₂ | 155–159 |
| CH₃ | C₂H₅ | OCH₂—CH=CH₂ | |

EXAMPLE 8

Preparation of 7-(difluoromethoxy)-2-isopropyl-2-methyl-5H-imidazo[1'2':1,2]pyrrolo[3,4-b]pyridine-3(2H), 5-dione Dicyclohexylcarbodiimide (1.07 g, 5 mmol) in 20 mL CH₂Cl₂ is added to a stirred solution containing 1.54 g (4.7 mmol) 5-(difluoromethoxy)-2-(4-isopropyl-4-methyl-5-oxo-2-imidazolin-2-yl)nicotinic acid in 30 mL CH₂Cl₂ under nitrogen at room temperature. The mixture is stirred overnight, filtered and concentrated to give the product, 7-(difluoromethoxy)-2-isopropyl-2- methyl-5H-imidazo[1',2':1,2]pyrrolo[3,4-b]pyridine-3(2H), 5-dione.

Using essentially the same conditions but substituting the appropriate substituted nicotinic acid for the difluoromethoxy derivative, the following compounds are prepared.

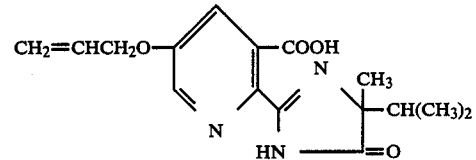

| X | Y | Z | R$_1$ | R$_2$ |
|---|---|---|---|---|
| H | OCF$_3$ | H | CH$_3$ | CH(CH$_3$)$_2$ |
| H | OCF$_2$CHF$_2$ | H | CH$_3$ | CH(CH$_3$)$_2$ |
| H | OCH$_2$CH=CH$_2$ | H | CH$_3$ | CH(CH$_3$)$_2$ |
| H | H | OCH$_2$CH=CH$_2$ | CH$_3$ | CH(CH$_3$)$_2$ |
| H | OCH$_2$C≡CH | H | CH$_3$ | CH(CH$_3$)$_2$ |
| H | H | OCH$_2$C≡CH | CH$_3$ | CH(CH$_3$)$_2$ |

EXAMPLE 9

Preparation of 7-alkyloxy-3-isopropyl-3-methyl-5H-imidazo[1',2',:1,2-]pyrrolo[3,4-b]pyridine-2-(3H),5-dione

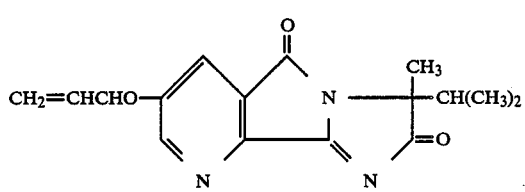

A solution containing 1.0 g 5-allyloxy-nicotinic acid and derivative in 10 mL toluene containing 1 mL acetic anhydride is heated under reflux for two hours. The solution is concentrated in vacuo to give the desired pyridone.

Using essentially the same procedure but substituting the appropriate nicotinic acid for the 5-allyloxy derivatives, the following compounds are prepared.

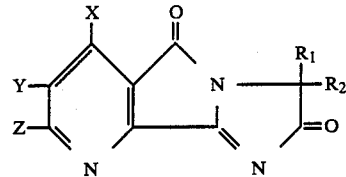

| X | Y | Z | R$_1$ | R$_2$ |
|---|---|---|---|---|
| H | OCH$_2$≡CH | H | CH$_3$ | CH(CH$_3$)$_2$ |
| H | OCH$_2$C=CH$_2$ Cl | H | CH$_3$ | CH(CH$_3$)$_2$ |
| H | OCH$_2$C=CH$_2$ CH$_3$ | H | CH$_3$ | CH(CH$_3$)$_2$ |
| H | H | OCH$_2$CH=CH$_2$ | CH$_3$ | CH(CH$_3$)$_2$ |
| H | OCHF$_2$ | H | CH$_3$ | CH(CH$_3$)$_2$ |
| H | OCF$_3$ | H | CH$_3$ | CH(CH$_3$)$_2$ |
| H | OCH$_2$CH=CHCH$_3$ | H | CH$_3$ | CH(CH$_3$)$_2$ |

EXAMPLE 10

Preparation of methyl 5-hydroxy-2-(4-isopropyl-4-methyl-5-oxo-2-imidazolin-2-yl)nicotinate-1-oxide

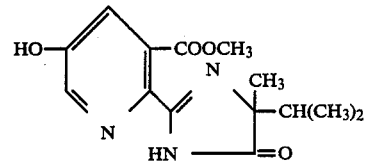

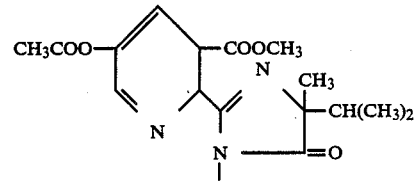

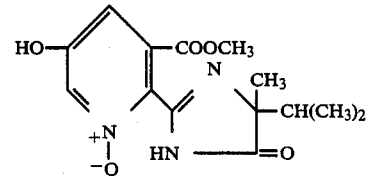

A solution containing 10 g methyl 5-hydroxy-2-(4-isopropyl-4-methyl-5-oxo-2-imidazolin-2-yl)nicotinate in 100 mL acetic anhydride is heated under reflux for 16 hours. The mixture is concentrated to give the crude diacetate which is dissolved in 125 mL methylene chloride and 6.52 g m-chloroperbenzoic acid added. After heating and reflux for 16 hours, excess per acid is destroyed by the addition of excess 1-hexane. The solution is washed with saturated sodium bicarbonate solution, dried and concentrated. The residue is dissolved in 100 mL methanol and 2.0 g sodium methoxide added. After stirring for two hours, the pH of the solution is adjusted to 7 with acetic acid, the mixture concentrated and the residue distributed between water and $CH_2Cl_2$. The extract is dried and concentrated to give the expected product, methyl 5-hydroxy-2-(4-isopropyl-4-methyl-5-oxo-2-imidazolin-2-yl)nicotinate-1-oxide.

EXAMPLE 11

Preparation of methyl 5-allyloxy-2-(4-isopropyl-4-methyl-5-thioxo-2-imidazolin-2-yl)nicotinate

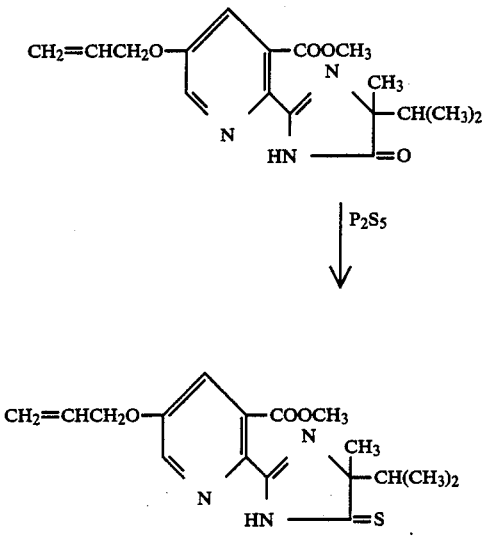

To a stirred suspension of 2.67 g $P_2S_5$ in 18 mL dioxane is added 3.31 g of the ester and the mixture heated under reflux for 24 hours. After cooling to room temperature, the mixture is concentrated in vacuo and 2.5 mL water added cautiously to the residue with stirring. The pH of the mixture is then adjusted to 8 with concentrated $NH_4OH$ whilst maintaining a temperature of approximately 35° C. The mixture is cooled and extracted with $CH_2Cl_2$, the extracts washed with water, dried and concentrated to give methyl 5-allyloxy-2-(4-isopropyl-4-methyl-5-thioxo-2-imidazolin-2-yl)nicotinate.

Using essentially the same procedure but reacting the appropriate 5-oxo derivative procedure with $P_2S_5$, the following compounds are prepared.

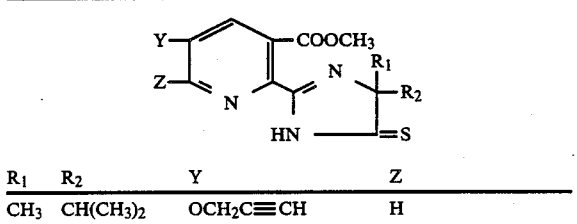

| $R_1$ | $R_2$ | Y | Z |
|---|---|---|---|
| $CH_3$ | $CH(CH_3)_2$ | $OCH_2C\equiv CH$ | H |
| $CH_3$ | $CH(CH_3)_2$ | $OCH_2C=CH_2$<br>$\mid$<br>$CH_3$ | H |
| $CH_3$ | $CH(CH_3)_2$ | $OCHF_2$ | H |
| $CH_3$ | $CH(CH_3)_2$ | $OCH_2-C=CH_2$<br>$\mid$<br>$Cl$ | H |
| $CH_3$ | $CH(CH_3)_2$ | $CF_2CHF_2$ | H |
| $CH_3$ | $CH(CH_3)_2$ | H | $OCH_2CH=CH_2$ |
| $CH_3$ | $CH(CH_3)_2$ | H | $OCH_2\equiv CH$ |
| $CH_3$ | $C_2H_5$ | $OCH_2CH=CH_2$ | H |
| $CH_3$ | $CH(CH_3)_2$ | $OCH_2CH=CHCH_3$ | H |

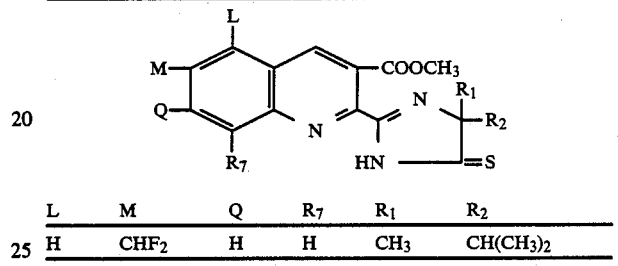

| L | M | Q | $R_7$ | $R_1$ | $R_2$ |
|---|---|---|---|---|---|
| H | $CHF_2$ | H | H | $CH_3$ | $CH(CH_3)_2$ |

EXAMPLE 12

Preparation of 5-trifluoromethoxy-2-pyridinecarboxylic acid

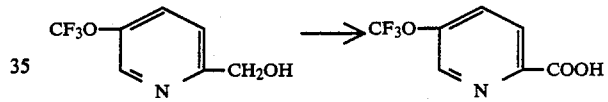

A mixture of 3 g 5-trifluoromethoxy-2-pyridinemethanol is vigorously stirred in 120 mL water at 5° C. To this mixture is added several portions 3.0 g potassium permanganate during which time the temperature rises to 25° C. After a further 30 minutes at 25° C., the mixture is filtered, the solid washed several times with water, the filtrate and washings combined and the pH adjusted to 5. The solution is concentrated to a small volume and extracted with ethyl acetate several times. The extract is washed, dried and concentrated to give 5-trifluoromethoxy-2-pyridinecarboxylic acid.

EXAMPLE 13

Preparation of 5-trifluoromethoxy-N-(1-carbamoyl-1,2-dimethylpropyl)picolinamide

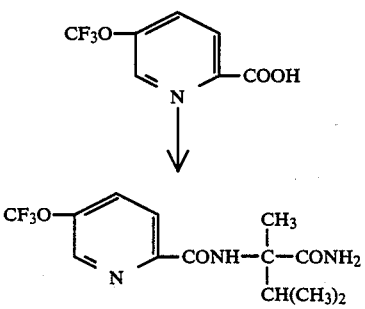

To a suspension of 2.31 g acid in 20 mL THF is added with stirring 1.07 mL ethyl chloroformate. The mixture is cooled to −10° C. and 1.71 mL triethylamine dropwise at such a rate that the temperature does not exceed 0° C. After ten minutes, a solution containing 1.43 g of 2-amino-2,3-dimethylbutyramide in 15 mL THF is added dropwise at 0° C. with stirring. The mixture is stirred at room temperature for two hours and enough water then added to dissolve the solids. The THF is removed in vacuo, the aqueous residue saturated with salt and extracted with ethyl acetate. The organic phase is separated, dried and concentrated to give 5-trifluoromethoxy-N-(1-carbamoyl-1,2-dimethylpropyl)-picolinamide.

EXAMPLE 14

Preparation of 2-(5-trifluoromethoxy-2-pyridyl)-4-isopropyl-4-methyl-2-imidazolin-5-one

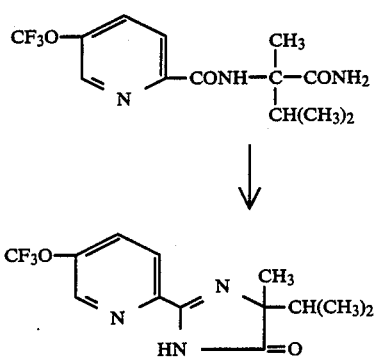

A stirred suspension of sodium hydride (0.24 g) in 25 mL toluene is heated under reflux under a Dean-Stark Water Separator. To this is added in small portions 2.9 g diamide. After the addition, heating is continued for one and one half hours. After standing overnight, the reaction is quenched with water, the pH adjusted to 5 and the phases separated. The aqueous phase is further extracted with ethyl acetate, the organic phases combined, washed with brine, dried and concentrated to give the product 2-(5-trifluoromethoxy-2-pyridyl)-4-isopropyl-4-methyl-2-imidazolin-5-one.

EXAMPLE 15

Preparation of 5-trifluoromethoxy-2-(4-isopropyl-4-methyl-5-oxo-2-imidazolin-2-yl)nicotinic acid

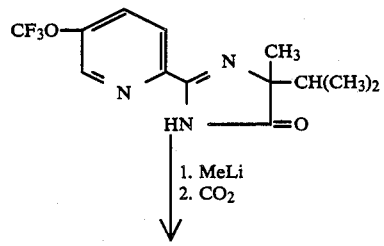

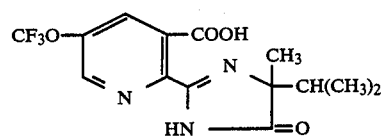

To a stirred solution containing 1.1 g imidazolinone in 10 mL THF at −76° C. under nitrogen is added dropwise 4.7 mL of a 1.7M solution of methyl lithium in ether. An additional 15 mL THF containing 0.25 mL hexamethylphosphoramide is added. The mixture is allowed to warm to −20° to −10° C. and held at this temperature for 0.75 hours. The mixture is cooled to −70° C. and added to a slurry of carbon dioxide in THF. After stirring for 0.5 hours, water is added, the pH adjusted to 2 with dilute sulfuric acid and the mixture extracted with methylene chloride. The extract is washed with brine, dried and concentrated to give the product, 5-trifluoromethoxy-2-(4-isopropyl-4-methyl-5-oxo-2-imidazolin-2-yl)nicotinic acid.

By substituting the appropriate α-aminocarboxamide for this carboxamide in Example 12 the following trifluoromethoxynicotinic acids are obtained.

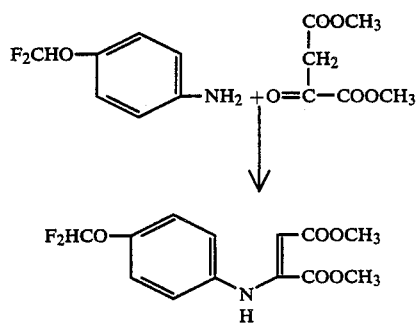

| $R_1$ | $R_2$ | W |
|---|---|---|
| $CH_3$ | $CH_3(CH_3)_2$ | S |
| $CH_3$ | $C_2H_5$ | O |
| $CH_3$ | Cyclopropyl | O |
| $CH_3$ | $CH_3$ | O |
| $CH_3$ | $C_2H_5$ | S |

EXAMPLE 16

Preparation of dimethyl 3-p-difluoromethoxyphenylaminobut-2-ene-dioate p-Difluoromethoxyaniline (0.217 mol) and dimethyl oxalacetate (0.217 mol) are mixed in toluene (500 mL) and heated under reflux under a Dean-Stark Water Separator for about one hour. The toluene is removed in vacuo to give dimethyl 3-p-difluoromethoxyphenylaminobut-2-ene-dioate as an oil.

EXAMPLE 17

Preparation of dimethyl 6-difluoromethoxyquinoline-2,3-dicarboxylate

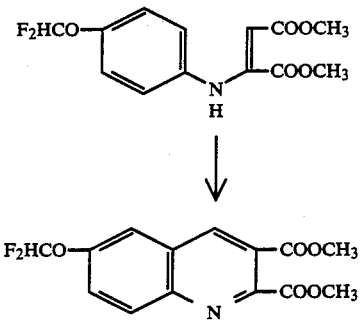

To a solution of dimethylformamide (0.1 mol) in ethylenedichloride (100 mL) cooled in an ice bath, is added dropwise, with stirring, phosphorous oxychloride (0.1 mol). The resulting solution is stirred at room temperature for one and one-half hours and then cooled again in an ice bath. To this solution is added dropwise a solution of dimethyl 3-p-difluoromethoxyphenylaminobut-2-ene-dioate (0.1 mol) in ethylene dichloride. The mixture is then heated under reflux for three hours, cooled and washed with half saturated brine. The organic phase is separated, dried and concentrated to give dimethyl 6-difluoromethoxyquinoline-2,3-dicarboxylate, mp 84°–85° C.

EXAMPLE 18

Preparation of 6-difluoromethoxyquinoline-2,3-dicarboxylic acid

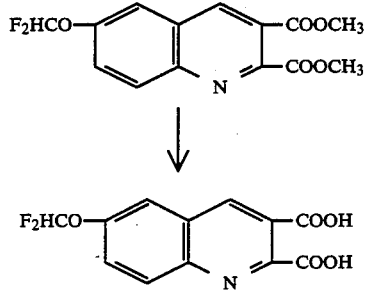

To a solution containing dimethyl 6-difluoromethoxyquinoline-2,3-dicarboxylate (0.162 mol) in 150 mL ethanol is added a solution of sodium hydroxide (0.5 mol) in 400 mL water and the mixture heated at reflux for five hours. The ethanol is removed in vacuo. The residue cooled to 5° C. and acidified with concentrated HCl. The product is removed by filtration, washed with water and dried to give 6-difluoromethoxyquinoline-2,3-dicarboxylic acid mp 226° C.

EXAMPLE 19

Preparation of 6-difluoromethoxyquinoline-2,3-dicarboxylic acid anhydride

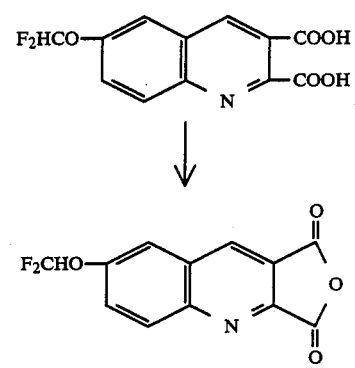

A mixture of 6-difluoromethoxyquinoline-2,3-dicarboxylic acid (0.14 mol) in 125 mL acetic anhydride is heated at 85° C. for one-half hour and then at 100° C. for one hour. The mixture is cooled, then filtered and the solids washed with ether to give 6-difluoromethoxyquinoline-2,3-dicarboxylic acid anhydride mp 157.5°–158.5° C.

EXAMPLE 20

Preparation of 6-difluoromethoxy-2-[(1-carbamoyl-1,2-dimethylpropyl)carbamoyl]-3-quinolinecarboxylic acid

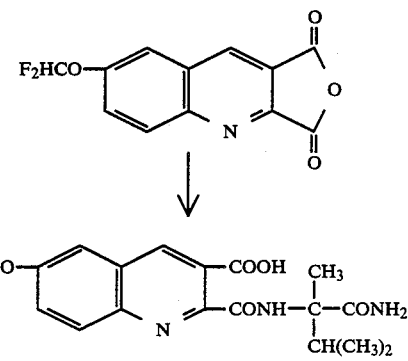

A solution of 6-difluoromethoxyquinoline-2,3-dicarboxylic acid anhydride (0.037 mol) in 250 mL THF is stirred at 5° C. under nitrogen and a solution containing 2-amino-2,3-dimethylbutyramide (0.037 mol) in 50 mL THF added dropwise. After stirring at room temperature for 17 hours, the solvent is removed in vacuo to give the desired 6-difluoromethoxy-2-[(1-carbamoyl-1,2-dimethylpropyl)-carbamoyl]-3-quinolinecarboxylic acid mp 194°–196° C.

EXAMPLE 21

Preparation of 6-difluoromethoxy-2-(4-isopropyl-4-methyl-5-oxo-2-imidazolin-2-yl)-3-quinolinecarboxylic acid

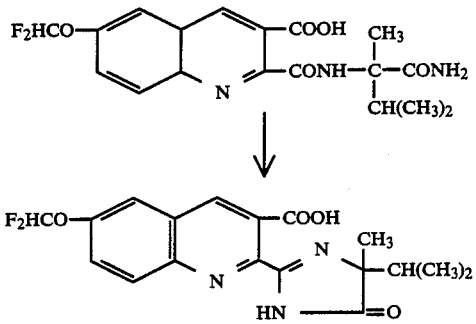

A solution of 6-difluoromethoxy-2-[(1-carbamoyl-1,2-dimethylpropyl)-carbamoyl]-3-quinolinecarboxylic acid (0.0152 mol) in 50 mL water containing 0.06 mol sodium hydroxide is heated at 75°–80° C. for two hours. The solution is cooled to 5° C. and acidified with concentrated HCl. The precipitate is removed by filtration, washed with water and air-dried to give 6-difluoromethoxy-2-(4-isopropyl-4-methyl-5-oxo-2-imidazolin-2-yl)-3-quinolinecarboxylic acid, mp 208°–209° C.

Following essentially the same procedures as described in Examples 8–13 but using the appropriately substituted aniline for difluoromethoxyaniline and the appropriate α-aminocarboxamide or α-aminothiocarboxamide for 2-amino-2,3-dimethylbutyramide, yields the compounds illustrated below.

| $R_1$ | $R_2$ | L | M | Q | $R_7$ | W | mp °C. |
|---|---|---|---|---|---|---|---|
| $CH_3$ | $CH(CH_3)_2$ | H | H | H | $OCHF_2$ | O | |
| $CH_3$ | $CH(CH_3)_2$ | H | H | $OCHF_2$ | H | O | |
| $CH_3$ | $C_2H_5$ | H | $OCHF_2$ | H | H | O | |
| $CH_3$ | Cyclopropyl | H | $OCHF_2$ | H | H | O | |
| $CH_3$ | $CH(CH_3)_2$ | H | H | $OCF_2CHF_2$ | H | O | |
| $CH_3$ | $CH(CH_3)_2$ | H | $OCF_2CHF_2$ | H | H | O | |
| $CH_3$ | $C_2H_5$ | H | $OCF_2CHF_2$ | H | H | O | |
| $CH_3$ | $CH(CH_3)_2$ | H | $OCF_3$ | H | H | O | 207.0–210.0 |
| $CH_3$ | $CH(CH_3)_2$ | H | $OCHF_2$ | H | H | S | |

EXAMPLE 22

Postemergence Herbicidal Evaluation of Test Compounds

The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN® 20, a polyoxyethylene sorbitan monolaurate surfactant of Atlas Chemical Industries, in sufficient quantity to provide the equivalent of about 0.016 kg of 10 kg per hectare of active compound when applied to the plants through a spray nozzle operating at 40 psig for a predetermined time. After spraying, the plants are placed on greenhouse benches and are cared for in the usual manner, commensurate with conventional greenhouse practices. From four to five weeks after treatment, the seedling plants, are examined and rated according to the rating system provided below. The data obtained are recorded in Table XI below.

| Rating System | % Difference in Growth from the Check |
|---|---|
| 0 - No Effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth, that is, a definite physiological malformation but with an over-all effect less than a 5 on the rating scale. | |

In most cases the data are for a single test, but in several instances, they are average values obtained from more than one test.

| Plant Species Used | |
|---|---|
| Barnyardgrass | (*Echinochloa crusgalli*) |
| Green foxtail | (*Setaria viridis*) |
| Purple Nutsedge | (*Cyperus rotundus* L.) |
| Wild Oats | (*Avena fatua*) |
| Quackgrass | (*Agropyron repens*) |
| Field Bindweed | (*Convolvulus arvensis* L.) |
| Cocklebur | (*Xanthium pensylvanicum*) |
| Morningglory | (*Ipomoea purpurea*) |
| Ragweed | (*Ambrosia artemisiifolia*) |
| Velvetleaf | (*Abutilon theophrasti*) |
| Barley | (*Hordeum vulgare*) |
| Corn | (*Zea mays*) |
| Rice | (*Oryza Sativa*) |
| Soybean | (*Glycine max*) |
| Sunflower | (*Helianthus annus*) |
| Wheat | (*Triticum aestivum*) |

TABLE I

POST-EMERGENCE TESTS - RATES IN KG/HA

| Compound | RATE | BARN-YARD-GR | FOX-TAIL SP | P NUT SEDGE | WILD OATS | QUACK GRASS | FLD BIND-WD | MATRI CARIA | MRN-GLRY SP | RAG-WEED | VELVET-LEAF | SUGAR BEETS | CORN FIELD | COT-TON | RICE NATO | SOY-BEAN BR |
|---|---|---|---|---|---|---|---|---|---|---|---|---|---|---|---|---|
| 6-(Difluoromethoxy)-2-(4-isopropyl)-4-methyl-5-oxo-2-imidazolin-2-yl)-3-quinolinecarboxylic acid | 1.000 | 9.0 | 9.0 | 0.0 | 9.0 | 7.0 | 9.0 | 8.0 | 9.0 | 9.0 | 4.0 | 9.0 | 9.0 | 9.0 | 7.0 | 3.0 |
| | .500 | 8.0 | 9.0 | 0.0 | 9.0 | 4.0 | 4.0 | 6.0 | 8.0 | | 3.0 | 9.0 | 9.0 | 7.0 | 6.0 | 1.0 |
| | .250 | 8.0 | 9.0 | 0.0 | 9.0 | 4.0 | 1.0 | 5.0 | 7.0 | | 1.0 | 9.0 | 9.0 | 9.0 | 5.0 | 1.0 |
| | .125 | 6.0 | 7.0 | 0.0 | 8.0 | 1.0 | | 2.0 | 6.0 | | 1.0 | 9.0 | 9.0 | 9.0 | 4.0 | 1.0 |
| | .063 | 5.0 | 5.0 | 0.0 | 6.0 | 1.0 | | 0.0 | 4.0 | | 0.0 | 7.0 | 9.0 | 7.0 | 2.0 | 1.0 |
| | .032 | 1.0 | 4.0 | 0.0 | 6.0 | 0.0 | | 0.0 | 4.0 | | 0.0 | 7.0 | 7.0 | 6.0 | 1.0 | 0.0 |
| 6-(Trifluoromethoxy)-2-(4-isopropyl)-4-methyl-5-oxo-2-imidazolin-2-yl)-3-quinolinecarboxylic acid | 1.000 | 9.0 | 9.0 | 0.0 | 9.0 | 0.0 | 0.0 | 6.0 | 2.0 | 3.0 | 0.0 | 9.0 | 9.0 | 2.0 | 7.0 | 3.0 |
| | .500 | 3.0 | 9.0 | 0.0 | 9.0 | 7.0 | 0.0 | 0.0 | 4.0 | 9.0 | 0.0 | 7.0 | 9.0 | 1.0 | 7.0 | 2.0 |
| | .250 | 1.0 | 9.0 | 0.0 | 8.0 | 6.0 | | 4.0 | 2.0 | 9.0 | 0.0 | 9.0 | 9.0 | 1.0 | 6.0 | 2.0 |
| | .125 | 1.0 | 9.0 | 0.0 | 7.0 | 4.0 | | 4.0 | 0.0 | 8.0 | 0.0 | 9.0 | 9.0 | 0.0 | 4.0 | 2.0 |
| | .063 | 0.0 | 6.0 | 0.0 | 3.0 | 2.0 | | 2.0 | 0.0 | 6.0 | 0.0 | 9.0 | 9.0 | 0.0 | 2.0 | 1.0 |
| | .032 | 0.0 | 0.0 | 0.0 | 4.0 | 2.0 | 0.0 | 0.0 | 0.0 | 0.0 | 0.0 | 7.0 | 6.0 | 0.0 | 2.0 | 1.0 |
| 2-(4-Isopropyl)-4-methyl-5-oxo-2-imidazolin-2-yl)-6-(2-propynyl-oxy)nicotinic acid | 1.000 | 9.0 | 9.0 | 7.0 | 9.0 | 7.0 | 7.0 | 8.0 | 9.0 | 8.0 | 9.0 | 9.0 | 9.0 | 8.0 | 9.0 | 8.0 |
| | .500 | 9.0 | 9.0 | 7.0 | 9.0 | 6.0 | | 8.0 | 8.0 | 7.0 | 7.0 | 9.0 | 8.0 | 8.0 | 7.0 | 8.0 |
| | .250 | 9.0 | 9.0 | 6.0 | 7.0 | 6.0 | 4.0 | 6.0 | 8.0 | 3.0 | 6.0 | 9.0 | 8.0 | 8.0 | 7.0 | 7.0 |
| | .125 | 8.0 | 8.0 | 6.0 | 7.0 | 6.0 | 3.0 | 3.0 | 7.0 | 2.0 | 3.0 | 8.0 | 7.0 | 8.0 | 7.0 | 6.0 |
| | .063 | 3.0 | 6.0 | 2.0 | 7.0 | 4.0 | 1.0 | 3.0 | 6.0 | 1.0 | 2.0 | 4.0 | 7.0 | 8.0 | 6.0 | 4.0 |
| | .032 | 1.0 | 4.0 | 1.0 | 3.0 | 1.0 | 0.0 | 0.0 | 3.0 | 0.0 | 0.0 | 4.0 | 4.0 | 4.0 | 4.0 | 2.0 |
| 6-(Allyloxy)-2-(4-isopropyl-4-methyl-5-oxo-2-imidazolin-2-yl)nicotinic acid | 1.000 | 9.0 | 9.0 | 7.0 | 9.0 | 9.0 | 7.0 | 6.0 | 9.0 | 9.0 | 9.0 | 9.0 | 9.0 | 9.0 | 8.0 | 7.0 |
| | .500 | 9.0 | 9.0 | 7.0 | 9.0 | 9.0 | 7.0 | 6.0 | 8.0 | 4.0 | 7.0 | 9.0 | 9.0 | 9.0 | 9.0 | 4.0 |
| | .250 | 7.0 | 9.0 | 4.0 | 9.0 | 9.0 | 6.0 | 6.0 | 9.0 | 3.0 | 6.0 | 9.0 | 9.0 | 9.0 | 6.0 | 3.0 |
| | .125 | 3.0 | 9.0 | 4.0 | 9.0 | 3.0 | | 2.0 | 9.0 | 1.0 | 5.0 | 8.0 | 9.0 | 9.0 | 5.0 | 5.0 |
| | .063 | 1.0 | 2.0 | 0.0 | 6.0 | 0.0 | 2.0 | 2.0 | 8.0 | 0.0 | 2.0 | 8.0 | 9.0 | 7.0 | 5.0 | 5.0 |
| | .032 | 0.0 | 0.0 | 0.0 | 0.0 | 0.0 | 0.0 | 0.0 | 3.0 | 0.0 | 0.0 | 4.0 | 4.0 | 4.0 | 3.0 | 4.0 |
| Methyl 6-(allyloxy)-2-(4-isopropyl-4-methyl-5-oxo-2-imidazolin-2-yl)nicotinate | 1.000 | 8.0 | 9.0 | 2.0 | 9.0 | 7.0 | 7.0 | 8.0 | 9.0 | 4.0 | 0.0 | 9.0 | 9.0 | 9.0 | 9.0 | 4.0 |
| | .500 | 4.0 | 8.0 | 5.0 | 8.0 | 4.0 | 2.0 | 2.0 | 6.0 | 3.0 | 7.0 | 9.0 | 9.0 | 6.0 | 5.0 | 3.0 |
| | .250 | 2.0 | 6.0 | 3.0 | 4.0 | 3.0 | 1.0 | 0.0 | 3.0 | 2.0 | 6.0 | 7.0 | 7.0 | 5.0 | 3.0 | 2.0 |
| | .125 | 0.0 | 2.0 | 0.0 | 3.0 | 1.0 | 0.0 | 0.0 | 2.0 | 0.0 | 2.0 | 4.0 | 5.0 | 2.0 | 2.0 | 1.0 |
| | .063 | 0.0 | 0.0 | 0.0 | 0.0 | 0.0 | 0.0 | 0.0 | 0.0 | 0.0 | 0.0 | 2.0 | 3.0 | 0.0 | 1.0 | 0.0 |
| | .032 | 0.0 | 0.0 | 0.0 | 0.0 | 0.0 | 0.0 | 0.0 | 0.0 | 0.0 | 0.0 | 2.0 | 2.0 | 0.0 | 1.0 | 0.0 |
| 5-(Allyloxy)-2-(4-isopropyl-4-methyl-5-oxo-2-imidazolin-2-yl)nicotinic acid | 1.000 | 9.0 | 9.0 | 2.0 | 8.0 | 7.0 | 9.0 | 8.0 | 9.0 | 9.0 | 9.0 | 9.0 | 9.0 | 9.0 | 7.0 | 6.0 |
| | .500 | 9.0 | 9.0 | 1.0 | 7.0 | 4.0 | 2.0 | 2.0 | 6.0 | 4.0 | 9.0 | 9.0 | 9.0 | 9.0 | 6.0 | 3.0 |
| | .250 | 8.0 | 9.0 | 1.0 | 6.0 | 3.0 | 1.0 | 0.0 | 3.0 | 3.0 | 7.0 | 7.0 | 9.0 | 9.0 | 4.0 | 3.0 |
| | .125 | 8.0 | 9.0 | 1.0 | 5.0 | 1.0 | 0.0 | 3.0 | 7.0 | 2.0 | 6.0 | 7.0 | 9.0 | 9.0 | | 3.0 |
| | .063 | 7.0 | 9.0 | 1.0 | 5.0 | 0.0 | 0.0 | 0.0 | 5.0 | 0.0 | 4.0 | 7.0 | 9.0 | 2.0 | 4.0 | 2.0 |
| | .032 | 4.0 | 8.0 | 0.0 | 0.0 | 0.0 | 0.0 | 0.0 | 2.0 | 0.0 | 2.0 | 4.0 | 3.0 | 0.0 | 3.0 | 1.0 |
| Methyl 5-(allyloxy)-2-(4-isopropyl-4-methyl-5-oxo-2-imidazolin-2-yl)nicotinate | 1.000 | 8.0 | 9.0 | 0.0 | 9.0 | 9.0 | 9.0 | 7.0 | 9.0 | 9.0 | 7.0 | 9.0 | 9.0 | 9.0 | 7.0 | 6.0 |
| | .500 | 7.0 | 9.0 | 0.0 | 9.0 | 9.0 | 9.0 | 5.0 | 7.0 | 7.0 | 4.0 | 9.0 | 9.0 | 9.0 | 7.0 | 6.0 |
| | .250 | 3.0 | 7.0 | 0.0 | 6.0 | 9.0 | 9.0 | 0.0 | 8.0 | 2.0 | 2.0 | 9.0 | 9.0 | 9.0 | 5.0 | 5.0 |
| | .125 | 1.0 | 5.0 | 0.0 | 3.0 | 9.0 | 9.0 | 1.0 | 6.0 | 1.0 | 1.0 | 8.0 | 6.0 | 7.0 | 3.0 | 3.0 |
| | .632 | 0.0 | 4.0 | 0.0 | 1.0 | 2.0 | 2.0 | 0.0 | 0.0 | 0.0 | 0.0 | 7.0 | 3.0 | 6.0 | 2.0 | 1.0 |
| | .032 | 0.0 | 2.0 | 0.0 | 0.0 | 0.0 | 2.0 | 0.0 | 0.0 | 0.0 | 0.0 | 4.0 | 2.0 | 3.0 | 1.0 | 1.0 |
| 5-(Difluoromethoxy)-2-(4-isopropyl-4-methyl-5-oxo-2-imidazolin-2-yl)nicotinic acid | 1.000 | 9.0 | 9.0 | 9.0 | 9.0 | 9.0 | 9.0 | 9.0 | 9.0 | 9.0 | 9.0 | 9.0 | 9.0 | 9.0 | 8.0 | 9.0 |
| | .500 | 9.0 | 9.0 | 7.0 | 9.0 | 9.0 | 9.0 | 9.0 | 9.0 | 9.0 | 9.0 | 9.0 | 9.0 | 9.0 | 8.0 | 8.0 |
| | .250 | 9.0 | 9.0 | 7.0 | 9.0 | 9.0 | 9.0 | 9.0 | 8.0 | 8.0 | 9.0 | 9.0 | 9.0 | 9.0 | 8.0 | 9.0 |
| | .125 | 9.0 | 9.0 | 6.0 | 9.0 | 9.0 | 7.0 | 9.0 | 9.0 | 2.0 | 9.0 | 9.0 | 9.0 | 9.0 | 8.0 | 6.0 |
| | .063 | 9.0 | 9.0 | 5.0 | 9.0 | 9.0 | 4.0 | 9.0 | 9.0 | 4.0 | 9.0 | 9.0 | 9.0 | 9.0 | 8.0 | 7.0 |
| | .032 | 9.0 | 9.0 | 6.0 | 9.0 | 9.0 | 7.0 | 7.0 | 9.0 | 7.0 | 9.0 | 9.0 | 9.0 | 7.0 | 8.0 | 3.0 |
| Methyl 2-(4-isopro- | 1.000 | 9.0 | 9.0 | 0.0 | 9.0 | 9.0 | 0.0 | 8.0 | 9.0 | | 9.0 | 9.0 | 9.0 | 8.0 | 8.0 | 7.0 |

TABLE I-continued

POST-EMERGENCE TESTS - RATES IN KG/HA

| Compound | RATE | BARN-YARD-GR | FOX-TAIL SP | P NUT SEDGE | WILD OATS | QUACK GRASS | FLD BIND-WD | MATRI CARIA | MRN-GLRY SP | RAG-WEED | VELVET-LEAF | SUGAR BEETS | CORN FIELD | COT-TON | RICE NATO | SOY-BEAN BR |
|---|---|---|---|---|---|---|---|---|---|---|---|---|---|---|---|---|
| pyl-4-methyl-5-oxo-2-imidazolin-2-yl)-5-(2-propynyloxy)-nicotinate | .500 | 8.0 | 9.0 | 3.0 | 9.0 | 9.0 | 9.0 | 6.0 | 9.0 | 5.0 | 7.0 | 9.0 | 9.0 | 9.0 | 7.0 | 5.0 |
|  | .250 | 5.0 | 9.0 | 1.0 | 9.0 | 5.0 | 9.0 | 6.0 | 9.0 | 3.0 | 5.0 | 9.0 | 9.0 | 9.0 | 7.0 | 3.0 |
|  | .125 | 5.0 | 9.0 | 1.0 | 6.0 | 3.0 | 9.0 | 3.0 | 4.0 | 2.0 | 3.0 | 9.0 | 9.0 | 7.0 | 6.0 | 3.0 |
|  | .063 | 0.0 | 8.0 | 0.0 | 0.0 | 0.0 | 8.0 | 0.0 | 2.0 | 0.0 | 0.0 | 6.0 | 8.0 | 7.0 | 5.0 | 2.0 |
|  | .032 | 0.0 | 7.0 | 0.0 | 0.0 | 0.0 | 7.0 | 0.0 | 0.0 | 0.0 | 0.0 | 8.0 | 5.0 | 6.0 |  | 1.0 |
| 2-(4-Isopropyl-4-methyl-5-oxo-2-imidazolin-2-yl)-5-(2-propynyloxy)nicotinic acid | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 | 8.0 |
|  | .500 | 9.0 | 9.0 | 9.0 | 9.0 | 9.0 | 9.0 | 9.0 | 9.0 | 9.0 | 9.0 | 9.0 | 9.0 | 9.0 | 9.0 | 7.0 |
|  | .250 | 9.0 | 9.0 | 9.0 | 9.0 | 9.0 | 9.0 | 9.0 | 9.0 | 8.0 | 9.0 | 9.0 | 9.0 | 8.0 | 9.0 | 6.0 |
|  | .125 | 9.0 | 9.0 | 6.0 | 9.0 | 8.0 | 9.0 | 5.0 | 9.0 | 6.0 | 9.0 | 9.0 | 9.0 | 9.0 | 9.0 | 6.0 |
|  | .063 | 9.0 | 9.0 | 3.0 | 9.0 | 8.0 | 9.0 | 5.0 | 9.0 | 6.0 | 9.0 | 9.0 | 9.0 | 5.0 | 8.0 | 4.0 |
|  | .032 | 9.0 | 9.0 | 0.0 | 9.0 | 5.0 | 9.0 | 2.0 | 8.0 | 2.0 | 6.0 | 9.0 | 9.0 | 8.0 | 8.0 | 2.0 |
| 2-(4-Isopropyl-4-methyl-5-oxo-2-imidazolin-2-yl)-5-[(2-methylallyl)oxy]-nicotinic acid | 1.000 | 9.0 |  | 1.5 | 9.0 | 8.5 | 9.0 | 9.0 | 8.5 |  | 9.0 | 9.0 | 9.0 | 8.0 |  | 1.0 |
|  | .500 | 8.5 |  | 0.5 | 9.0 | 8.5 | 9.0 | 8.5 | 5.5 |  | 9.0 | 9.0 | 9.0 | 8.0 |  | 0.0 |
|  | .250 | 6.0 |  | 0.0 | 7.5 | 7.5 | 9.0 | 4.5 | 3.5 |  | 9.0 | 7.5 | 9.0 | 6.0 |  | 0.0 |
|  | .125 | 3.0 |  | 0.0 | 6.5 | 7.5 | 9.0 | 3.5 | 2.0 |  | 5.5 | 5.5 | 9.0 | 4.0 |  | 0.0 |
|  | .063 | 1.5 |  | 0.0 | 3.0 | 2.0 | 9.0 | 0.5 | 1.0 |  | 3.0 | 3.0 | 6.0 | 1.0 |  | 0.0 |
|  | .032 | 0.0 |  | 0.0 | 1.0 | 0.0 | 8.0 | 0.0 | 0.0 |  | 2.5 | 2.0 | 4.0 | 0.5 |  | 0.0 |
| Methyl 2-(4-isopropyl-4-methyl-5-oxo-2-imidazolin-2-yl)-5-[(2-methylallyl)oxy]nicotinate | 1.000 | 0.0 |  | 0.0 | 2.0 | 8.0 | 9.0 | 4.0 | 4.0 |  | 7.0 | 0.0 | 3.0 | 3.0 |  | 0.0 |
|  | .500 | 0.0 |  | 0.0 | 2.0 | 6.0 | 9.0 | 3.0 | 2.0 |  | 8.0 | 0.0 | 3.0 | 3.0 |  | 0.0 |
|  | .250 | 0.0 |  | 0.0 | 2.0 | 2.0 | 9.0 | 3.0 | 1.0 |  | 2.0 | 0.0 | 3.0 | 3.0 |  | 0.0 |
|  | .125 | 0.0 |  | 0.0 | 0.0 | 0.0 | 9.0 | 2.0 | 0.0 |  | 0.0 | 0.0 | 1.0 | 1.0 |  | 0.0 |
|  | .063 | 0.0 |  | 0.0 | 0.0 | 0.0 | 4.0 | 0.0 | 0.0 |  | 0.0 | 0.0 | 2.0 | 0.5 |  | 0.0 |
|  | .032 | 0.0 |  | 0.0 | 0.0 | 0.0 | 0.0 | 0.0 | 0.0 |  | 0.0 | 0.0 | 0.0 | 0.0 |  | 0.0 |
| 5-(2-Butenyloxy)-2-(4-isopropyl-4-methyl-5-oxo-2-imidazolin-2-yl)nicotinic acid | 1.000 | 9.0 |  | 7.0 | 9.0 | 9.0 | 9.0 | 7.0 | 6.0 | 8.0 | 9.0 | 9.0 | 9.0 | 6.0 |  | 3.0 |
|  | .500 | 9.0 |  | 4.0 | 9.0 | 9.0 | 9.0 | 4.0 | 4.0 | 4.0 | 9.0 | 9.0 | 9.0 | 6.0 |  | 1.0 |
|  | .250 | 6.0 |  | 1.0 | 9.0 | 8.0 | 9.0 | 0.0 | 2.0 | 2.0 | 9.0 | 9.0 | 9.0 | 2.0 |  | 1.0 |
|  | .125 | 3.0 |  | 1.0 | 9.0 | 2.0 | 9.0 | 0.0 | 0.0 | 0.0 | 4.0 | 9.0 | 9.0 | 2.0 |  | 1.0 |
|  | .063 | 0.0 |  | 1.0 | 9.0 | 2.0 | 8.0 | 0.0 | 0.0 | 0.0 | 4.0 | 9.0 | 7.0 | 2.0 |  | 0.0 |
|  | .032 | 0.0 |  | 0.0 | 6.0 | 0.0 | 4.0 | 0.0 | 0.0 | 0.0 | 0.0 | 9.0 | 4.0 | 0.0 |  | 0.0 |
| Methyl 5-[(2-chloroalkyl)oxy]-2-(4-isopropyl-4-methyl-5-oxo-2-imidazolin-2-yl)nicotinate | 1.000 | 7.0 |  | 0.0 | 8.0 | 6.0 | 9.0 | 8.0 | 7.0 | 6.0 | 9.0 | 9.0 | 8.0 | 7.0 |  | 2.0 |
|  | .500 | 4.0 |  | 0.0 | 6.0 | 2.0 | 9.0 | 0.0 | 4.0 | 2.0 | 8.0 | 4.0 | 7.0 | 2.0 |  | 0.0 |
|  | .250 | 1.0 |  | 0.0 | 2.0 | 2.0 | 9.0 | 0.0 | 2.0 | 0.0 | 6.0 | 2.0 | 4.0 | 0.0 |  | 0.0 |
|  | .125 | 0.0 |  | 0.0 | 2.0 | 0.0 | 9.0 | 0.0 | 0.0 | 0.0 | 2.0 | 1.0 | 2.0 | 0.0 |  | 0.0 |
|  | .063 | 0.0 |  | 0.0 | 0.0 | 0.0 | 8.0 | 0.0 | 0.0 | 0.0 | 0.0 | 0.0 | 2.0 | 0.0 |  | 0.0 |
|  | .032 | 0.0 |  | 0.0 | 0.0 | 0.0 | 4.0 | 0.0 | 0.0 | 0.0 | 0.0 | 0.0 | 2.0 | 0.0 |  | 0.0 |
| 5-[(2-chloroallyl)oxy]-2-(4-isopropyl-4-methyl-5-oxo-2-imidazolin-2-yl)-nicotinic acid | 1.000 | 9.0 |  | 7.0 | 9.0 | 9.0 | 9.0 | 9.0 | 9.0 | 9.0 | 9.0 | 9.0 | 9.0 | 8.0 |  | 3.0 |
|  | .500 | 9.0 |  | 6.0 | 9.0 | 9.0 | 9.0 | 9.0 | 8.0 | 9.0 | 9.0 | 9.0 | 9.0 | 8.0 |  | 2.0 |
|  | .250 | 9.0 |  | 4.0 | 9.0 | 9.0 | 9.0 | 9.0 | 8.0 | 9.0 | 9.0 | 9.0 | 9.0 | 9.0 |  | 1.0 |
|  | .125 | 6.0 |  | 2.0 | 9.0 | 4.0 | 9.0 | 6.0 | 4.0 | 6.0 | 8.0 | 9.0 | 9.0 | 7.0 |  | 1.0 |
|  | .063 | 2.0 |  | 2.0 | 8.0 | 2.0 | 9.0 | 2.0 | 4.0 | 0.0 | 0.0 | 9.0 | 9.0 | 3.0 |  | 0.0 |
|  | .032 | 0.0 |  | 0.0 | 7.0 | 0.0 | 9.0 | 0.0 | 0.0 | 0.0 | 4.0 | 4.0 | 8.0 | 2.0 |  | 0.0 |

EXAMPLE 23

Preemergence Herbicidal Evaluation of Test Compounds

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.016 to 10 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth above. The herbicidal proficiency of the active ingredients of the present invention is evident from the test results which are recorded in Table XII below. Where more than one test is involved for a given compound, the data are averaged.

TABLE I

PRE-EMERGENCE TESTS - RATES IN KG/HA

| Compound | RATE | BARN-YARD GR | FOX-TAIL SP | P NUT SEDGE | WILD OATS | CRACK GRASS | FLD BIND WD | MATRI CARIA | MRN-GLRY SP | RAG-WEED | VELVET LEAF | SUGAR BEETS | CORN FIELD | COT-TON | RICE NATO | SOY-BEAN BR |
|---|---|---|---|---|---|---|---|---|---|---|---|---|---|---|---|---|
| 6-(Difluoromethoxy)-2-(4-Isopropyl-4-methyl-5-oxo-2-imidazolin-2-yl)-3-quinolinecarboxylic acid | .500 | 2.0 | 9.0 | 0.0 | 9.0 | 9.0 | 6.0 | 4.0 | 5.0 | 8.0 | 4.0 | 9.0 | 9.0 | 9.0 | 9.0 | 3.0 |
| | .250 | 0.0 | 9.0 | 0.0 | 7.0 | 8.0 | 5.0 | 1.0 | 2.0 | 6.0 | 1.0 | 9.0 | 9.0 | 9.0 | 9.0 | |
| | .125 | 0.0 | 9.0 | 0.0 | 7.0 | 8.0 | 3.0 | 0.0 | 1.0 | | 0.0 | 9.0 | 9.0 | 0.0 | 7.0 | |
| | .063 | 0.0 | 3.0 | 0.0 | 6.0 | 7.0 | 1.0 | 0.0 | 0.0 | | 0.0 | 9.0 | 3.0 | 0.0 | 6.0 | 0.0 |
| | .032 | 0.0 | 0.0 | 0.0 | 3.0 | 5.0 | 0.0 | 0.0 | 0.0 | 0.0 | 0.0 | 9.0 | 1.0 | 0.0 | 0.0 | 0.0 |
| | .016 | 0.0 | 0.0 | 0.0 | 1.0 | 0.0 | 0.0 | 0.0 | 0.0 | 0.0 | 0.0 | 6.0 | 0.0 | 0.0 | 0.0 | 0.0 |
| 6-(Trifluoromethoxy)-2-(4-isopropyl-4-methyl-5-oxo-2-imidazolin-2-yl)-3-quinolinecarboxylic acid | .500 | 9.0 | 9.0 | 2.0 | 9.0 | 9.0 | 9.0 | 9.0 | 9.0 | 9.0 | 8.0 | 9.0 | 9.0 | 9.0 | 9.0 | 3.0 |
| | .250 | 5.0 | 8.0 | 1.0 | 9.0 | 9.0 | 9.0 | 8.0 | 9.0 | 9.0 | 7.0 | 9.0 | 9.0 | 9.0 | 9.0 | 3.0 |
| | .125 | 4.0 | 9.0 | 0.0 | 9.0 | 9.0 | 7.0 | 8.0 | 8.0 | 9.0 | 5.0 | 9.0 | 9.0 | 5.0 | 8.0 | 3.0 |
| | .063 | 0.0 | 8.0 | 0.0 | 6.0 | 7.0 | 2.0 | 6.0 | 6.0 | 9.0 | 3.0 | 9.0 | 9.0 | 2.0 | 6.0 | 2.0 |
| | .032 | 0.0 | 1.0 | 0.0 | 4.0 | 6.0 | 1.0 | 4.0 | 5.0 | | 2.0 | 8.0 | 8.0 | 1.0 | 2.0 | 1.0 |
| | .016 | 0.0 | 0.0 | 0.0 | 1.0 | 2.0 | 0.0 | 1.0 | 1.0 | | 1.0 | 8.0 | 0.0 | 0.0 | 1.0 | 0.0 |
| 2-(4-Isopropyl-4-methyl-5-oxo-2-imidazolin-2-yl)-6-(2-propynyl-oxy)nicotinic acid | .500 | 7.0 | 9.0 | 9.0 | 9.0 | 9.0 | 9.0 | 9.0 | 9.0 | 9.0 | 7.0 | 9.0 | 9.0 | 9.0 | 9.0 | 8.0 |
| | .250 | 5.0 | 8.0 | 9.0 | 9.0 | 9.0 | 9.0 | 9.0 | 9.0 | 9.0 | 7.0 | 9.0 | 9.0 | 9.0 | 9.0 | 5.0 |
| | .125 | 2.0 | 6.0 | 8.0 | 3.0 | 9.0 | 8.0 | 0.0 | 4.0 | 4.0 | 5.0 | 9.0 | 6.0 | 6.0 | 8.0 | 3.0 |
| | .063 | 0.0 | 1.0 | 7.0 | 1.0 | 2.0 | 6.0 | 0.0 | 4.0 | 4.0 | 2.0 | 8.0 | 3.0 | 2.0 | 3.0 | 1.0 |
| | .032 | 0.0 | 0.0 | 4.0 | 0.0 | 2.0 | 5.0 | 0.0 | 1.0 | | 0.0 | 7.0 | 1.0 | 1.0 | 2.0 | 1.0 |
| | .016 | 0.0 | 0.0 | 0.0 | 0.0 | 1.0 | 0.0 | 0.0 | 0.0 | 0.0 | 0.0 | 7.0 | 0.0 | 0.0 | 0.0 | 0.0 |
| 6-(Allyloxy)-2-(4-isopropyl-4-methyl-5-oxo-2-imidazolin-2-yl)nicotinic acid | .500 | 9.0 | 9.0 | 9.0 | 9.0 | 9.0 | 9.0 | 9.0 | 9.0 | 9.0 | 9.0 | 9.0 | 9.0 | 9.0 | 9.0 | 7.0 |
| | .250 | 4.0 | 9.0 | 9.0 | 8.0 | 9.0 | 8.0 | 4.0 | 9.0 | 9.0 | 8.0 | 9.0 | 9.0 | 9.0 | 9.0 | 5.0 |
| | .125 | 4.0 | 7.0 | 9.0 | 8.0 | 8.0 | 9.0 | 2.0 | 7.0 | 6.0 | 8.0 | 9.0 | 6.0 | 9.0 | 8.0 | 4.0 |
| | .063 | 2.0 | 4.0 | 9.0 | 2.0 | 7.0 | 8.0 | 0.0 | 3.0 | 0.0 | 7.0 | 8.0 | 6.0 | 6.0 | 8.0 | 3.0 |
| | .032 | 0.0 | 4.0 | 4.0 | 0.0 | 2.0 | 0.0 | 0.0 | 2.0 | 0.0 | 4.0 | 8.0 | 3.0 | 2.0 | 4.0 | 2.0 |
| | .016 | 0.0 | 0.0 | 0.0 | 0.0 | 0.0 | 0.0 | 0.0 | 0.0 | 0.0 | 0.0 | 3.0 | 0.0 | 2.0 | 3.0 | 2.0 |
| Methyl 6-(allyloxy)-2-(4-isopropyl-4-methyl-5-oxo-2-imidazolin-2-yl)nicotinate | .500 | 9.0 | 9.0 | 8.0 | 9.0 | 9.0 | 4.0 | 4.0 | 9.0 | 9.0 | 8.0 | 9.0 | 7.0 | 7.0 | 6.0 | 3.0 |
| | .250 | 9.0 | 8.0 | 6.0 | 8.0 | 7.0 | 2.0 | 1.0 | 8.0 | 9.0 | 7.0 | 9.0 | 5.0 | 4.0 | 3.0 | 2.0 |
| | .125 | 6.0 | 7.0 | 4.0 | 7.0 | 3.0 | 1.0 | 0.0 | 4.0 | 0.0 | 5.0 | 9.0 | 3.0 | 2.0 | 3.0 | 2.0 |
| | .063 | 2.0 | 3.0 | 2.0 | 4.0 | 3.0 | 1.0 | 0.0 | 1.0 | 0.0 | 2.0 | 9.0 | 3.0 | 2.0 | 3.0 | 2.0 |
| | .032 | 1.0 | 1.0 | 0.0 | 1.0 | 1.0 | 0.0 | 0.0 | 0.0 | 0.0 | 1.0 | 7.0 | 2.0 | 1.0 | 2.0 | |
| | .016 | 0.0 | 0.0 | 0.0 | 0.0 | 0.0 | 0.0 | 0.0 | 0.0 | 0.0 | 0.0 | 4.0 | 2.0 | 1.0 | 0.0 | 2.0 |
| 5-(Allyloxy)-2-(4-isopropyl-4-methyl-5-oxo-2-imidazolin-2-yl)nicotinic acid | .500 | 9.0 | 9.0 | 8.0 | 9.0 | 9.0 | 9.0 | 9.0 | 8.3 | 9.0 | 9.0 | 9.0 | 9.0 | 8.7 | 9.0 | 2.0 |
| | .250 | 8.7 | 9.0 | 7.0 | 8.0 | 9.0 | 9.0 | 8.0 | 8.0 | 5.0 | 9.0 | 9.0 | 9.0 | 7.3 | 9.0 | 2.0 |
| | .125 | 8.0 | 7.0 | 6.0 | 7.0 | 9.0 | 9.0 | 4.0 | 7.3 | 7.0 | 8.0 | 9.0 | 9.0 | 4.7 | 8.0 | |
| | .063 | 6.3 | 8.0 | 4.5 | 3.0 | 9.0 | 9.0 | 3.0 | 5.3 | 2.0 | 8.0 | 7.0 | 9.0 | 3.0* | 9.0 | 0.0 |
| | .032 | 4.7* | 7.0 | 0.5 | 1.0 | 5.0 | 7.5 | 1.0 | 0.7 | 1.0 | 6.0 | 9.0 | 6.0 | 4.0* | 6.0 | 1.0 |
| | .016 | 2.7* | 3.0 | 0.0 | 0.0 | 4.0 | 7.5 | 0.0 | 0.0 | 0.0 | 4.0 | 9.0 | 3.0 | 3.0* | 6.0 | |
| Methyl 5-(allyloxy)-2-(4-isopropyl-4-methyl-5-oxo-2-imidazolin-2-yl)nicotinate | .500 | 9.0 | 9.0 | 7.0 | 9.0 | 9.0 | 9.0 | 9.0 | 9.0 | 9.0 | 9.0 | 4.0 | 9.0 | 8.0 | 6.0 | 0.0 |
| | .250 | 8.0 | 9.0 | 5.0 | 8.0 | 9.0 | 9.0 | 6.0 | 8.0 | 8.0 | 9.0 | 9.0 | 9.0 | | 9.0 | 2.0 |
| | .125 | 7.0 | 9.0 | 2.0 | 6.0 | 9.0 | 8.0 | 6.0 | 4.0 | 6.0 | 9.0 | 9.0 | 9.0 | 3.0 | 9.0 | 0.0 |
| | .063 | 5.0 | 8.0 | 1.0 | 2.0 | 9.0 | 6.0 | 4.0 | 2.0 | 5.0 | 7.0 | 7.0 | 8.0 | | 8.0 | 0.0 |
| | .032 | 2.0 | 3.0 | 0.0 | 1.0 | 9.0 | 6.0 | 0.0 | 0.0 | 0.0 | 3.0 | | 3.0 | 0.0 | 3.0 | 0.0 |
| | .016 | 0.0 | 1.0 | 0.0 | 0.0 | | 0.0 | 0.0 | 0.0 | 0.0 | 1.0 | 7.0 | 2.0 | 0.0 | 2.0 | 0.0 |
| 5-(Difluoromethyl)-2-(4-isopropyl-4-methyl-5-oxo-2-imidazolin-2-yl)nicotinic acid | .500 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 8.0 | 8.0 | 9.0 | 9.0 | 9.0 | 9.0 | 9.0 | 9.0 |
| | .125 | 8.0 | 8.0 | 9.0 | 9.0 | 9.0 | 9.0 | 9.0 | 7.3 | 7.0 | 9.0 | 9.0 | 9.0 | 9.0 | 9.0 | 9.0 |
| | .063 | 8.0 | 8.0 | 8.0 | 9.0 | 9.0 | 9.0 | 8.0 | 5.3 | 6.0 | 8.0 | 9.0 | 9.0 | 9.0 | 9.0 | 7.0 |
| | .032 | 6.0 | 7.0 | 7.0 | 9.0 | 7.0 | 9.0 | 6.0 | 6.0 | 8.0 | 8.0 | 9.0 | 9.0 | 8.0 | 7.0 | 5.0 |
| | .016 | 2.0 | 7.0 | 7.0 | 6.0 | 7.0 | 6.0 | 2.0 | 6.0 | 7.0 | 8.0 | 9.0 | 9.0 | 9.0 | 5.0 | 2.0 |
| Methyl 2-(4-isopro- | .500 | 9.0 | 9.0 | 9.0 | 9.0 | 9.0 | 9.0 | 9.0 | 8.0 | 8.0 | 9.0 | 9.0 | 9.0 | 9.0 | 9.0 | 3.0 |

TABLE I-continued

PRE-EMERGENCE TESTS - RATES IN KG/HA

| Compound | RATE | BARN-YARD GR | FOX-TAIL SP | P NUT SEDGE | WILD OATS | CRACK GRASS | FLD BIND WD | MATRI CARIA | MRN-GLRY SP | RAG-WEED | VELVET LEAF | SUGAR BEETS | CORN FIELD | COT-TON | RICE NATO | SOY-BEAN BR |
|---|---|---|---|---|---|---|---|---|---|---|---|---|---|---|---|---|
| pyl-4-methyl-5-oxo-2-imidazolin-2-yl)-5-(2-propynyloxy)-nicotinate | .250 | 9.0 | 9.0 | 9.0 | 8.0 | 9.0 | 9.0 | 8.0 | 7.0 | 8.0 | 8.0 | 9.0 | 9.0 | 8.0 | 9.0 | 2.0 |
|  | .125 | 8.0 | 9.0 | 8.0 | 2.0 | 7.0 | 9.0 | 2.0 | 4.0 | 5.0 | 8.0 | 9.0 | 9.0 | 7.0 | 9.0 | 2.0 |
|  | .063 | 7.0 | 8.0 | 8.0 | 0.0 | 5.0 | 9.0 | 0.0 | 4.0 | 5.0 | 8.0 | 9.0 | 9.0 | 7.0 | 6.0 | 2.0 |
|  | .032 | 7.0 | 6.0 | 5.0 | 0.0 | 3.0 | 9.0 | 0.0 | 0.0 | 0.0 | 6.0 | 8.0 | 2.0 | 3.0 | 6.0 | 1.0 |
|  | .016 | 0.0 | 0.0 | 0.0 | 0.0 | 0.0 | 3.0 | 0.0 | 0.0 | 0.0 | 0.0 | 4.0 | 2.0 | 0.0 | 2.0 | 1.0 |
| 2-(4-Isopropyl-4-methyl-5-oxo-2-imidazolin-2-yl)-5-(2-propynyloxy)nicotinic acid | .500 | 9.0 | 9.0 | 9.0 | 9.0 | 9.0 | 9.0 | 9.0 | 9.0 | 9.0 | 9.0 | 9.0 | 9.0 | 9.0 | 9.0 | 6.0 |
|  | .250 | 9.0 | 9.0 | 9.0 | 9.0 | 9.0 | 9.0 | 9.0 | 9.0 | 9.0 | 8.0 | 9.0 | 9.0 | 8.0 | 9.0 | 4.0 |
|  | .125 | 8.0 | 9.0 | 7.0 | 8.0 | 9.0 | 9.0 | 8.0 | 7.0 | 7.0 | 8.0 | 9.0 | 9.0 | 7.0 | 9.0 | 3.0 |
|  | .063 | 9.0 | 9.0 | 6.0 | 7.0 | 9.0 | 9.0 | 6.0 | 5.0 | 3.0 | 8.0 | 9.0 | 9.0 | 4.0 | 9.0 | 2.0 |
|  | .032 | 7.0 | 6.0 | 0.0 | 0.0 | 9.0 |  | 0.0 | 2.0 | 0.0 | 7.0 | 9.0 | 7.0 | 4.0 | 7.0 | 2.0 |
|  | .016 |  |  | 0.0 |  | 0.0 | 0.0 |  |  |  |  |  |  |  |  |  |
| 2-(4-Isopropyl-4-methyl-5-oxo-2-imidazolin-2-yl)-5-[(2-methylallyl)oxy]-nicotinic acid | .500 | 9.0 |  | 3.0 | 7.5 | 9.0 | 9.0 | 7.0 | 8.0 | 8.0 | 8.5 | 9.0 | 8.0 | 8.5 |  | 1.0 |
|  | .250 | 7.0 |  | 2.0 | 6.0 | 8.5 | 7.5 | 4.5 | 6.5 | 8.0 | 8.5 | 6.5 | 8.0 | 4.0 |  | 0.5 |
|  | .125 | 4.5 |  | 0.5 | 3.0 | 4.0 | 4.0 | 3.0 | 5.0* | 6.5 | 7.5 | 4.5 | 7.0 | 1.5 |  | 0.0 |
|  | .063 | 1.5 |  | 0.0 | 1.0 | 1.5 | 2.0 | 1.5 | 2.5 | 3.0 | 5.5 | 2.0 | 3.5 | 1.0 |  | 0.0 |
|  | .032 | 0.5 |  | 0.0 | 1.0 | 0.0 | 1.0 | 0.0 | 0.0 | 1.0 | 2.0 | 1.0 | 2.5 | 0.0 |  | 0.0 |
|  | .016 | 0.0 |  | 0.0 | 0.0 | 0.0 | 0.0 | 0.0 | 0.0 | 0.0 | 0.0 | 0.0 | 2.5 | 0.0 |  | 0.0 |
| Methyl 2-(4-isopropyl-4-methyl-5-oxo-2-imidazolin-2-yl)-5-[(2-methylallyl)-oxy]nicotinate | .500 | 9.0 |  | 2.0 | 4.0 | 8.0 | 8.0 | 9.0 | 6.0 | 8.0 | 8.0 | 8.0 | 7.0 | 3.0 |  | 2.0 |
|  | .250 | 6.0 |  | 1.0 | 2.0 | 7.0 | 8.0 | 5.0 | 8.0 | 7.0 | 3.0 | 4.0 | 5.0 | 2.0 |  | 2.0 |
|  | .125 | 2.0 |  | 0.0 | 1.0 | 6.0 | 4.0 | 2.0 | 4.0 | 2.0 | 1.0 | 3.0 | 3.0 | 0.0 |  | 1.0 |
|  | .063 | 0.0 |  | 0.0 | 0.0 | 2.0 | 2.0 | 0.0 | 2.0 | 0.0 | 0.0 | 3.0 | 2.0 | 0.0 |  | 0.0 |
|  | .032 | 0.0 |  | 0.0 | 0.0 | 0.0 | 0.0 | 0.0 | 0.0 | 0.0 | 0.0 | 0.0 | 2.0 | 0.0 |  | 0.0 |
|  | .016 | 0.0 |  | 0.0 | 0.0 | 0.0 | 0.0 | 0.0 | 0.0 | 0.0 | 0.0 | 0.0 | 0.0 | 0.0 |  | 0.0 |
| 5-(2-Butenloxy)-2-(4-isopropyl-4-methyl-5-oxo-2-imidazolin-2-yl)nicotinic acid | .500 | 9.0 |  | 4.0 | 7.0 | 9.0 | 9.0 | 2.0 | 4.0 | 6.0 | 7.0 | 9.0 | 9.0 | 6.0 |  | 3.0 |
|  | .250 | 7.0 |  | 2.0 | 5.0 | 7.0 | 8.0 | 1.0 | 2.0 | 4.0 | 5.0 | 7.0 | 7.0 | 2.0 |  | 0.0 |
|  | .125 | 3.0 |  | 0.0 | 3.0 | 5.0 | 4.0 | 0.0 | 0.0 | 4.0 | 4.0 | 3.0 | 5.0 | 0.0 |  | 0.0 |
|  | .063 | 0.0 |  | 0.0 | 2.0 | 2.0 | 2.0 | 0.0 | 0.0 | 2.0 | 0.0 | 2.0 | 3.0 | 0.0 |  | 0.0 |
|  | .032 | 0.0 |  | 0.0 | 0.0 | 0.0 | 0.0 | 0.0 | 0.0 | 0.0 | 0.0 | 0.0 | 2.0 | 0.0 |  | 0.0 |
|  | .016 | 0.0 |  | 0.0 | 0.0 | 0.0 | 0.0 | 0.0 | 0.0 | 0.0 | 0.0 | 0.0 | 0.0 | 0.0 |  | 0.0 |
| Methyl 5-[(2-chloroalkyl)oxy]-2-(4-isopropyl-4-methyl-5-oxo-2-imidazolin-2-yl)nicotinate | .500 | 9.0 |  | 0.0 | 2.0 | 9.0 | 9.0 | 8.0 | 6.0 | 8.0 | 9.0 | 8.0 | 8.0 | 7.0 |  | 3.0 |
|  | .250 | 8.0 |  | 0.0 | 2.0 | 9.0 | 9.0 | 7.0 | 4.0 | 8.0 | 6.0 | 9.0 | 8.0 | 1.0 |  | 0.0 |
|  | .125 | 7.0 |  | 0.0 | 2.0 | 7.0 | 9.0 | 5.0 | 2.0 | 2.0 | 3.0 | 5.0 | 5.0 | 1.0 |  | 0.0 |
|  | .063 | 3.0 |  | 0.0 | 1.0 | 5.0 | 6.0 | 3.0 | 0.0 | 2.0 | 3.0 | 5.0 | 2.0 | 0.0 |  | 0.0 |
|  | .032 | 0.0 |  | 0.0 | 0.0 | 4.0 | 4.0 | 0.0 | 0.0 | 0.0 | 2.0 | 4.0 | 1.0 | 0.0 |  | 0.0 |
|  | .016 | 0.0 |  | 0.0 | 0.0 | 2.0 | 2.0 | 0.0 | 0.0 | 0.0 | 0.0 | 2.0 | 0.0 | 0.0 |  | 0.0 |
| 5-[(2-chloroallyl)oxy]-2-(4-isopropyl-4-methyl-5-oxo-2-imidazolin-2-yl)-nicotinic acid | .500 | 9.0 |  | 2.0 | 9.0 | 9.0 | 9.0 | 8.0 | 9.0 | 9.0 | 9.0 | 8.0 | 8.0 | 7.0 |  | 1.0 |
|  | .250 | 9.0 |  | 4.0 | 7.0 | 9.0 | 9.0 | 8.0 | 8.0 | 9.0 | 8.0 | 9.0 | 8.0 | 3.0 |  | 1.0 |
|  | .125 | 6.0 |  | 0.0 | 4.0 | 9.0 | 7.0 | 4.0 | 3.0 | 4.0 | 5.0 | 5.0 | 5.0 | 1.0 |  | 0.0 |
|  | .063 | 2.0 |  | 0.0 | 3.0 | 4.0 | 7.0 | 3.0 | 0.0 | 2.0 | 2.0 | 3.0 | 2.0 | 0.0 |  | 0.0 |
|  | .032 | 0.0 |  | 0.0 | 0.0 | 2.0 | 2.0 | 0.0 | 0.0 | 2.0 | 2.0 | 2.0 | 1.0 | 0.0 |  | 0.0 |
|  | .016 | 0.0 |  | 0.0 | 0.0 | 0.0 | 0.0 | 0.0 | 0.0 | 0.0 | 0.0 | 0.0 | 1.0 | 0.0 |  | 0.0 |

What is claimed is:
1. A compound of the formula:

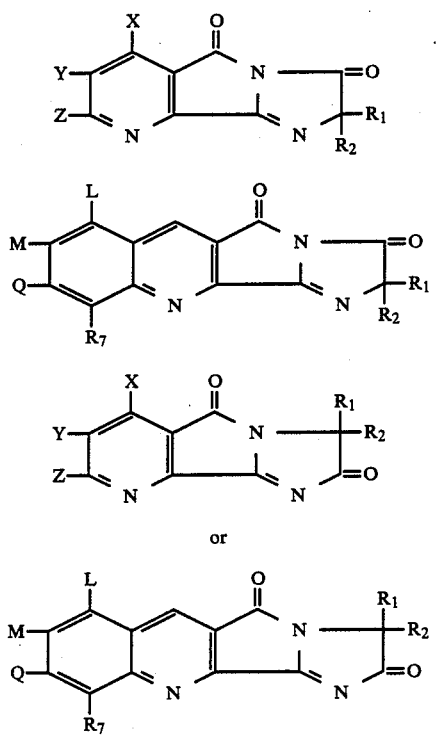

wherein
$R_1$ is $C_1$–$C_4$ alkyl;
$R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl;
X is hydrogen, halogen or methyl;
Y is hydrogen, halogen, $C_1$–$C_6$ alkyl, $C_1$–$C_4$ hydroxyloweralkyl, $C_1$–$C_6$ alkoxy, $C_1$–$C_4$ alkylthio, phenoxy, $C_1$–$C_4$ haloalkyl, nitro, cyano, $C_1$–$C_4$ alkylamino, di-$C_1$–$C_4$-loweralkylamino, $C_1$–$C_4$ alkylsulfonyl or phenyl optionally substituted with one $C_1$–$C_4$ alkyl, $C_1$–$C_4$ alkoxy or halogen, difluoromethoxy, trifluoromethoxy, 1,1,2,2-tetrafluoroethoxy, $C_3$–$C_8$ straight or branched alkenyloxy optionally substituted with one to three halogens, or $C_3$–$C_8$ straight or branched alkynyloxy optionally substituted with one to three halogens;
Z is hydrogen, halogen, $C_1$–$C_6$ alkyl, $C_1$–$C_4$ hydroxyloweralkyl, $C_1$–$C_6$ alkoxy, $C_1$–$C_4$ alkylthio, phenoxy, $C_1$–$C_4$ haloalkyl, nitro, cyano, $C_1$–$C_4$ alkylamino, di-$C_1$–$C_4$-loweralkylamino, $C_1$–$C_4$ alkylsulfonyl or phenyl optionally substituted with one $C_1$–$C_4$ alkyl or $C_1$–$C_4$ alkoxy or halogen, $C_3$–$C_8$ straight or branched alkenyloxy optionally substituted with one to three halogens, or $C_3$–$C_8$ straight or branched alkynyloxy optionally substituted with one to three halogens;
with the proviso that at least one of Y and Z is difluoromethoxy, trifluoromethoxy, 1,1,2,2-tetrafluoroethoxy, $C_3$–$C_8$ straight or branched alkenyloxy optionally substituted with one to three halogens, or $C_3$–$C_8$ straight or branched alkynyloxy optionally substituted with one to three halogens;
L, M, Q and $R_7$ each represent hydrogen, halogen, $C_1$–$C_4$ alkyl, $C_1$–$C_4$ alkoxy, $C_1$–$C_4$ alkylthio, $C_1$–$C_4$ alkylsulfonyl, $C_1$–$C_4$ haloalkyl, difluoromethoxy, trifluoromethoxy, 1,1,2,2,-tetrafluoroethoxy, $NO_2$, CN, phenyl, phenoxy, amino, $C_1$–$C_4$ alkylamino, diloweralkylamino, chlorophenyl, methylphenyl, phenoxy substituted with one Cl, $CF_3$, $NO_2$ or $CH_3$ group, $C_3$–$C_8$ straight or branched alkenyloxy optionally substituted with one to three halogens, or $C_3$–$C_8$ straight or branched alkynyloxy optionally substituted with one to three halogens; with the proviso that at least one of L, M, Q or $R_7$, is difluoromethoxy, trifluoromethoxy, 1,1,2,2-tetrafluoroethoxy, $C_3$–$C_8$ straight or branched alkenyloxy optionally substituted with one to three halogens, or $C_3$–$C_8$ straight or branched alkynyloxy optionally substituted with one to three halogens;
the N-oxides thereof provided that Y or Z cannot be alkylthio, dialkylamino or alkylamino;
the optical isomers thereof when $R_1$ and $R_2$ are not the same.
2. A compound according to claim 1, wherein $R_1$, and $R_2$ are as described in claim 1 and at least one of Y, Z, L, M, Q and $R_7$ is difluoromethoxy, trifluoromethoxy, 1,1,2,2-tetrafluoroethoxy, $OCH_2$—$CH$=$CH_2$, $OCH_2$—$C$≡$CCH_3$, $$OCH_2-\underset{CH_3}{\overset{|}{C}}=CH_2, \quad OCH_2-\underset{Cl}{\overset{|}{C}}=CH_2, \quad OCH_2-\underset{Cl}{\overset{|}{C}}=CHCl,$$

$OCH_2CH$=$CH_3$, $$OCH_2\underset{Cl}{\overset{|}{C}}=CCl_2$$

or $OCH_2$—$CH$=$CHCl$.
3. A method for the control of monocotyledonous and dicotyledonous annual, perennial and aquatic plant species comprising: applying to the foliage of said plants or to soil or water containing seeds or other propagating organs thereof, a herbicidally effective amount of a compound having a structure:

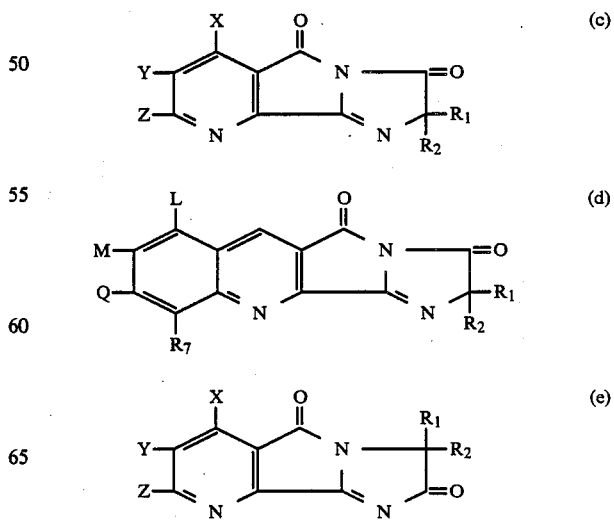

-continued

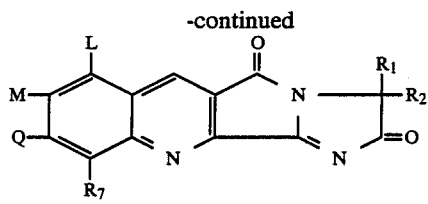
(f)

wherein
r₁ is $C_1$-$c_4$ alkyl;
$R_2$ is $C_1$-$C_4$ alkyl or $C_3$-$C_6$ cycloalkyl; and when $R_1$ and $R_2$ are taken together with the carbon to which they are attached they may represent $C_3$-$C_6$ cycloalkyl optionally substituted with methyl;
X is hydrogen, halogen, or methyl;
Y is hydrogen, halogen, $C_1$-$C_6$ alkyl, $C_1$-$C_4$ hydroxyloweralkyl, $C_1$-$C_6$ alkoxy, $C_1$-$C_4$ alkylthio, phenoxy, $C_1$-$C_4$ haloalkyl, nitro, cyano, $C_1$-$C_4$ alkylamino, di-$C_1$-$C_4$-loweralkylamino, $C_1$-$C_4$ alkylsulfonyl or phenyl optionally substituted with one $C_1$-$C_4$ alkyl, $C_1$-$C_4$ alkoxy or halogen, difluoromethoxy, trifluoromethoxy, 1,1,2,2-tetrafluoroethoxy, $C_3$-$C_8$ straight or branched alkenyloxy optionally substituted with one to three halogens, or $C_3$-$C_8$ straight or branched alkynyloxy optionally substituted with one to three halogens;
Z is hydrogen, halogen, $C_1$-$C_6$ alkyl, $C_1$-$C_4$ hydroxyloweralkyl, $C_1$-$C_6$ alkoxy, $C_1$-$C_4$ alkylthio, phenoxy, $C_1$-$C_4$ haloalkyl, nitro, cyano, $C_1$-$C_4$ alkylamino, di-$C_1$-$C_4$-loweralkylamino, $C_1$-$C_4$ alkylsulfonyl or phenyl optionally substituted with one $C_1$-$C_4$ alkyl or $C_1$-$C_4$ alkoxy or halogen, $C_3$-$C_8$ straight or branched alkenyloxy optionally substituted with one to three halogens, or $C_3$-$C_8$ straight or branched alkynyloxy optionally substituted with one to three halogens;
with the proviso that at least one of Y and Z is difluoromethoxy, trifluoromethoxy, 1,1,2,2-tetrafluoroethoxy, $C_3$-$C_8$ straight or branched alkenyloxy optionally substituted with one to three halogens, or $C_3$-$C_8$ straight or branched alkynyloxy optionally substituted with one to three halogens;
L, M, Q and $R_7$ each represent hydrogen, halogen, $C_1$-$C_4$ alkyl, $C_1$-$C_4$ alkoxy, $C_1$-$C_4$ alkylthio, $C_1$-$C_4$ alkylsulfonyl, $C_1$-$C_4$ haloalkyl, difluoromethoxy, trifluoromethoxy, 1,1,2,2-tetrafluoroethoxy, $NO_2$, ON, phenyl, phenoxy, amino, $C_1$-$C_4$ alkylamino, diloweralkylamino, chlorophenyl, methylphenyl, phenoxy substituted with one Cl, $CF_3$, $NO_2$ or $CH_3$ group, $C_3$-$C_8$ straight or branched alkenyloxy optionally substituted with one to three halogens, or $C_3$-$C_8$ straight or branched alkynyloxy optionally substituted with one to three halogens; with the proviso that at least one of L, M, Q or $R_7$, is difluoromethoxy, trifluoromethoxy, 1,1,2,2-tetrafluoroethoxy, $C_3$-$C_8$ straight or branched alkenyloxy optionally substituted with one to three halogens, or $C_3$-$C_8$ straight or branched alkynyloxy optionally substituted with one to three halogens;
the N-oxides thereof provided that Y or Z cannot be alkylamino, dialkylamino or alkylthio;
the optical isomers thereof when $R_1$ and $R_2$ are not the same.

4. The method according to claim 3, comprising applying an effective amount of a compound wherein at least one of Y, Z, L, M, Q and $R_7$ is difluoromethoxy, trifluoromethoxy, 1,1,2,2-tetrafluoroethoxy, $OCH_2$—CH=$CH_2$, $OCH_2$—C≡CH,

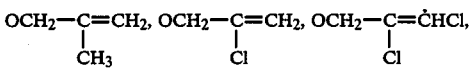

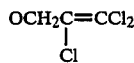

or $OCH_2$—CH=CHCl.

* * * * *